United States Patent
Matsumoto

(10) Patent No.: US 12,193,807 B2
(45) Date of Patent: *Jan. 14, 2025

(54) ACOUSTIC WAVE MEASUREMENT APPARATUS AND OPERATION METHOD OF ACOUSTIC WAVE MEASUREMENT APPARATUS

(71) Applicant: FUJIFILM Corporation, Tokyo (JP)

(72) Inventor: Tsuyoshi Matsumoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/516,546

(22) Filed: Nov. 21, 2023

(65) Prior Publication Data

US 2024/0081680 A1 Mar. 14, 2024

Related U.S. Application Data

(63) Continuation of application No. 16/793,569, filed on Feb. 18, 2020, now Pat. No. 11,864,883, which is a (Continued)

(30) Foreign Application Priority Data

Aug. 24, 2017 (JP) ................................ 2017-161262

(51) Int. Cl.
    *A61B 5/05* (2021.01)
    *A61B 5/00* (2006.01)
    (Continued)

(52) U.S. Cl.
    CPC ............ *A61B 5/107* (2013.01); *A61B 5/0095* (2013.01); *A61B 5/742* (2013.01); *A61B 5/746* (2013.01);
    (Continued)

(58) Field of Classification Search
    CPC .................................. A61B 5/746; A61B 5/742
    See application file for complete search history.

(56) References Cited

U.S. PATENT DOCUMENTS

| 6,454,712 B1 | 9/2002 | Oonuki |
| 10,426,438 B2 | 10/2019 | Roh et al. |

(Continued)

FOREIGN PATENT DOCUMENTS

| CN | 102131465 A | 7/2011 |
| CN | 105050504 A | 11/2015 |

(Continued)

OTHER PUBLICATIONS

Advisory Action issued in copending U.S. Appl. No. 16/793,569 on Apr. 11, 2022.

(Continued)

*Primary Examiner* — Joel F Brutus
(74) *Attorney, Agent, or Firm* — Birch, Stewart, Kolasch & Birch, LLP

(57) ABSTRACT

An acoustic wave measurement apparatus includes: an image display unit that displays an acoustic wave image; a measurement target designation receiving unit that receives designation of a measurement target; a position designation receiving unit that receives designation of a position of a measurement target on the acoustic wave image displayed on the image display unit; a measurement method information receiving unit that receives measurement method information indicating a measurement method; a detection measurement algorithm setting unit that sets a detection measurement algorithm based on the measurement target received by the measurement target designation receiving unit and the measurement method information received by the measurement method information receiving unit; and a measurement unit that detects the measurement target based on the received position and the detection measurement (Continued)

algorithm and performs measurement for the detected measurement target.

19 Claims, 16 Drawing Sheets

Related U.S. Application Data continuation of application No. PCT/JP2018/020680, filed on May 30, 2018.

(51) Int. Cl.
  *A61B 5/107* (2006.01)
  *A61B 8/00* (2006.01)
  *A61B 8/08* (2006.01)
(52) U.S. Cl.
  CPC ................ *A61B 8/085* (2013.01); *A61B 8/46* (2013.01); *A61B 8/5207* (2013.01)

(56) References Cited

U.S. PATENT DOCUMENTS

| | | | |
|---|---|---|---|
| 2005/0096543 | A1 | 5/2005 | Jackson et al. |
| 2011/0152687 | A1 | 6/2011 | Iimura et al. |
| 2011/0270087 | A1 | 11/2011 | Yoshida et al. |
| 2013/0116537 | A1 | 5/2013 | Sato |
| 2014/0046185 | A1 | 2/2014 | Mo et al. |
| 2015/0265247 | A1* | 9/2015 | Roh .................. A61B 8/465 |
| | | | 600/440 |
| 2015/0320399 | A1 | 11/2015 | Chono et al. |
| 2017/0112386 | A1 | 4/2017 | Irisawa |

FOREIGN PATENT DOCUMENTS

| | | | |
|---|---|---|---|
| CN | 107019525 | A | 8/2017 |
| EP | 2 921 115 | A1 | 9/2015 |
| JP | 5-127819 | A | 5/1993 |
| JP | 2000-185038 | A | 7/2000 |
| JP | 4220605 | B2 | 2/2009 |
| JP | 2010-148811 | A | 7/2010 |
| JP | 2010-240198 | A | 10/2010 |
| JP | 2013-111434 | A | 6/2013 |
| JP | 6055565 | B1 | 12/2016 |

OTHER PUBLICATIONS

Advisory Action issued in copending U.S. Appl. No. 16/793,569 on Feb. 13, 2023.
Chinese Office Action and Search Report for corresponding Chinese Application No. 201880054374.8, dated Mar. 1, 2022, with an English translation.
Extended European Search Report dated Jul. 6, 2020 for corresponding Application No. 18848310.1.
International Preliminary Report on Patentability and Written Opinion of the International Searching Authority with an English translation (forms PCT/IB/373, PCT/ISA/237 and PCT/IB/326), dated Mar. 5, 2020, for corresponding International Application No. PCT/JP2018/020680.
International Search Report (form PCT/ISA/210), dated Jul. 3, 2018, for corresponding International Application No. PCT/JP2018/020680, with an English translation.
Japanese Office Action dated Jun. 7, 2022 for corresponding Application No. 2021-091401, with an English translation.
Japanese Office Action for corresponding Japanese Application No. 2019-537935, dated Mar. 30, 2021, with English translation.
Japanese Office Action for corresponding Japanese Application No. 2019-537935, dated Sep. 28, 2021, with English translation.
Japanese Office Action, dated Nov. 10, 2020, for corresponding Japanese Application No. 2019-537935, with an English translation.
Notice of Allowance issued in copending U.S. Appl. No. 16/793,569 on Aug. 23, 2023.
Office Action issued in copending U.S. Appl. No. 16/793,569 on Apr. 28, 2023.
Office Action issued in copending U.S. Appl. No. 16/793,569 on Jan. 19, 2022.
Office Action issued in copending U.S. Appl. No. 16/793,569 on Jul. 21, 2021.
Office Action issued in copending U.S. Appl. No. 16/793,569 on May 16, 2022.
Office Action issued in copending U.S. Appl. No. 16/793,569 on Oct. 24, 2022.

\* cited by examiner

ACOUSTIC WAVE MEASUREMENT APPARATUS AND OPERATION METHOD OF ACOUSTIC WAVE MEASUREMENT APPARATUS

CROSS-REFERENCE TO RELATED APPLICATIONS

This application is a continuation of U.S. application Ser. No. 16/793,569, filed Feb. 18, 2020, which is a continuation of PCT International Application No. PCT/JP2018/020680 filed on May 30, 2018, which claims priority under 35 U.S.C § 119(a) to Patent Application No. 2017-161262 filed in Japan on Aug. 24, 2017, all of which are hereby expressly incorporated by reference in their entirety into the present application.

BACKGROUND OF THE INVENTION

1. Field of the Invention

The present invention relates to a medical image diagnostic apparatus using an acoustic wave, and relates to an acoustic wave measurement apparatus and an operation method of an acoustic wave measurement apparatus for measuring an organ, a lesion, and the like on an acoustic wave image displayed on a display device.

2. Description of the Related Art

In recent years, medical acoustic wave measurement apparatuses generally have a measurement function for measuring the length, area, and the like of various organs, lesions, and the like included in an acquired acoustic wave image. In order to measure a measurement target, an operator usually operates a caliper, that is, a cursor using an input device for inputting coordinates, such as a track pad, a track ball, and a mouse, to set a measurement point, a region of interest, and the like on a display image.

JP2010-240198A discloses an ultrasound diagnostic apparatus that allows the operator to concentrate on diagnosis without being confused by the operation by automatically determining the optimal measurement item according to the type of measurement target part, an image mode under measurement, and the setting order of measurement points input by the operator. JP2010-148811A discloses a technique for solving a problem that it is difficult to see an ultrasound diagnostic image or a measurement result by preventing contamination due to fingerprints adhering to display means by separately comprising display means for displaying an ultrasound diagnostic image and a display and reception means for giving an instruction for measurement processing.

SUMMARY OF THE INVENTION

In both JP2010-240198A and JP2010-148811A, since measurement points are input only by a manual input operation, it takes time or effort to align the measurement points with the measurement target. In addition, the operator may have variations in the input of measurement points, and the measurement results may also vary.

On the other hand, in a case where there are a plurality of measurement methods for one measurement target, for example, in a gallbladder short axis image, in a case where there are a method of measurement in the vertical direction and a method of measurement in the horizontal direction, the operator needs to designate a measurement method in advance, or it is necessary to perform measurement in all measurement methods and select a measurement result later. This requires time and effort.

The present invention has been made in view of such problems, and it is an object of the present invention to provide an acoustic wave measurement apparatus and an operation method of an acoustic wave measurement apparatus capable of measuring a measurement target quickly and easily with less effort and performing measurement with reduced variations by the operator by reducing the measurement method selection work or the measurement result selection work of the operator.

An acoustic wave measurement apparatus of the present invention comprises: an image display unit that displays an acoustic wave image; a measurement target designation receiving unit that receives designation of a measurement target; a position designation receiving unit that receives designation of a position of a measurement target on the acoustic wave image displayed on the image display unit; a measurement method information receiving unit that receives measurement method information indicating a measurement method; a detection measurement algorithm setting unit that sets a detection measurement algorithm based on the measurement target received by the measurement target designation receiving unit and the measurement method information received by the measurement method information receiving unit; and a measurement unit that detects the measurement target based on the position received by the position designation receiving unit and the detection measurement algorithm set by the detection measurement algorithm setting unit and performs measurement for the detected measurement target.

In the present invention, the "acoustic wave" is a term including an ultrasound wave and a photoacoustic wave. The "detection measurement algorithm" is an algorithm including an algorithm for detection and an algorithm for measurement.

In the present invention, the "measurement method" means which of the length, area, and the like of the measurement target is to be measured. In the case of measuring the length, the "measurement method" means in which direction the measurement is to be performed.

In the acoustic wave measurement apparatus of the present invention, reception of designation of the position of the measurement target by the position designation receiving unit and reception of the measurement method information by the measurement method information receiving unit may be separate.

In the acoustic wave measurement apparatus of the present invention, reception of designation of the position of the measurement target by the position designation receiving unit and reception of the measurement method information by the measurement method information receiving unit may be integrated.

In the acoustic wave measurement apparatus of the present invention, the measurement unit may determine a position of a detection range in which the detection is performed based on the position received by the position designation receiving unit.

In the present invention, the "detection range" means a region on the acoustic wave image on which detection processing is performed, and the "position of the detection range" means a position where the region is present.

In the acoustic wave measurement apparatus of the present invention, the measurement unit may determine a measurement position where the measurement is performed based on the position received by the position designation receiving unit.

In the present invention, the "measurement position" means a place where measurement points are arranged. As for the "measurement point", in the case of measuring the distance between two points in the measurement target, the two points are referred to as measurement points.

In the acoustic wave measurement apparatus of the present invention, in a case where there is only one measurement method capable of measuring the measurement target received by the measurement target designation receiving unit, the detection measurement algorithm setting unit neglects the measurement method information and sets the detection measurement algorithm based on the measurement method capable of measuring the measurement target.

In the present invention, the "measurement method capable of measuring the measurement target" means a measurement method set in advance for each measurement target.

The acoustic wave measurement apparatus of the present invention further comprises a notification unit that, in a case where there is only one measurement method capable of measuring the measurement target received by the measurement target designation receiving unit, provides notification of information indicating the measurement method capable of measuring the measurement target.

The acoustic wave measurement apparatus of the present invention further comprises a warning notification unit that gives a warning in a case where the detection measurement algorithm setting unit is not able to set a detection measurement algorithm based on the measurement method information received by the measurement method information receiving unit.

The acoustic wave measurement apparatus of the present invention acoustic may further comprise a detection condition setting unit that sets conditions, under which the detection for the measurement target is performed, based on at least one of the position received by the position designation receiving unit or the measurement target received by the measurement target designation receiving unit, and the measurement unit may perform detection based on the conditions set by the detection condition setting unit.

In the acoustic wave measurement apparatus of the present invention, the detection condition setting unit may determine at least one of a shape of a detection range, a size of the detection range, a detection accuracy, or a detection order as conditions for performing the detection.

In the acoustic wave measurement apparatus of the present invention, the acoustic wave image may be an ultrasound image.

In the acoustic wave measurement apparatus of the present invention, the acoustic wave image may be a photoacoustic wave image.

An operation method of an acoustic wave measurement apparatus of the present invention is an operation method of an acoustic wave measurement apparatus comprising an image display unit, a measurement target designation receiving unit, a position designation receiving unit, a measurement method information receiving unit, a detection measurement algorithm setting unit, and a measurement unit, and comprises: causing the image display unit that to display an acoustic wave image; causing the measurement target designation receiving unit to receive designation of a measurement target; causing the position designation receiving unit to receive designation of a position of a measurement target on the acoustic wave image displayed on the image display unit; causing the measurement method information receiving unit to receive measurement method information indicating a measurement method; causing the detection measurement algorithm setting unit to set a detection measurement algorithm based on the measurement target received by the measurement target designation receiving unit and the measurement method information received by the measurement method information receiving unit; and causing the measurement unit to detect the measurement target based on the position received by the position designation receiving unit and the detection measurement algorithm set by the detection measurement algorithm setting unit and perform measurement for the detected measurement target.

According to the acoustic wave measurement apparatus and the operation method of an acoustic wave measurement apparatus of the present invention, there are provided: the image display unit that displays an acoustic wave image; the measurement target designation receiving unit that receives designation of a measurement target; the position designation receiving unit that receives designation of a position of a measurement target on the acoustic wave image displayed on the image display unit; the measurement method information receiving unit that receives measurement method information indicating a measurement method; the detection measurement algorithm setting unit that sets a detection measurement algorithm based on the measurement target received by the measurement target designation receiving unit and the measurement method information received by the measurement method information receiving unit; and the measurement unit that detects the measurement target based on the position received by the position designation receiving unit and the detection measurement algorithm set by the detection measurement algorithm setting unit and performs measurement for the detected measurement target. Therefore, in a case where the operator designates the approximate position of the measurement target on the acoustic wave image displayed on the image display unit and inputs information indicating a measurement method such as a measurement direction, for example, inputs a straight line in the vertical direction or inputs a straight line in the horizontal direction, the measurement unit can automatically detect and measure a measurement target. In this manner, by reducing the measurement method selection work or the measurement result selection work of the operator, it is possible to measure the measurement target quickly and easily with less effort and perform measurement with reduced variations by the operator.

DESCRIPTION OF THE PREFERRED EMBODIMENTS

Figure 1:
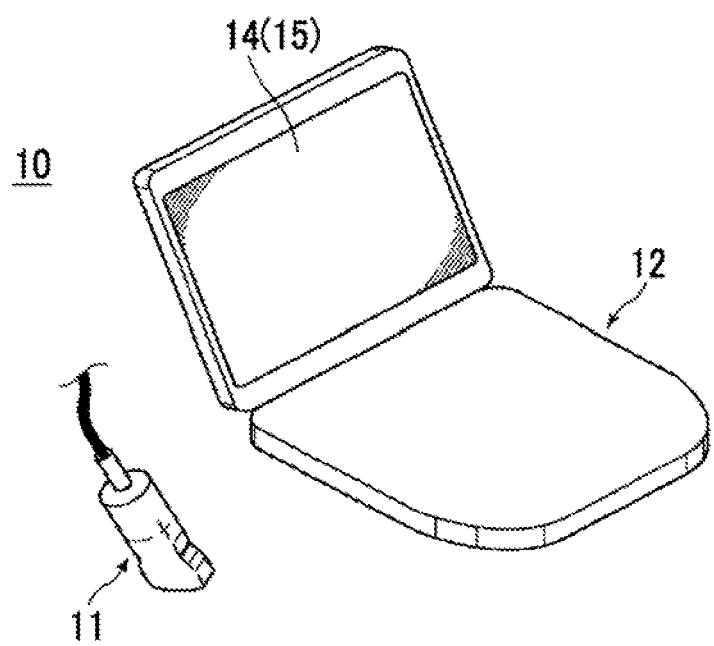
FIG. 1 is a perspective view showing an acoustic wave image capturing apparatus comprising an acoustic wave measurement apparatus according to a first embodiment of the present invention.
Figure 2:
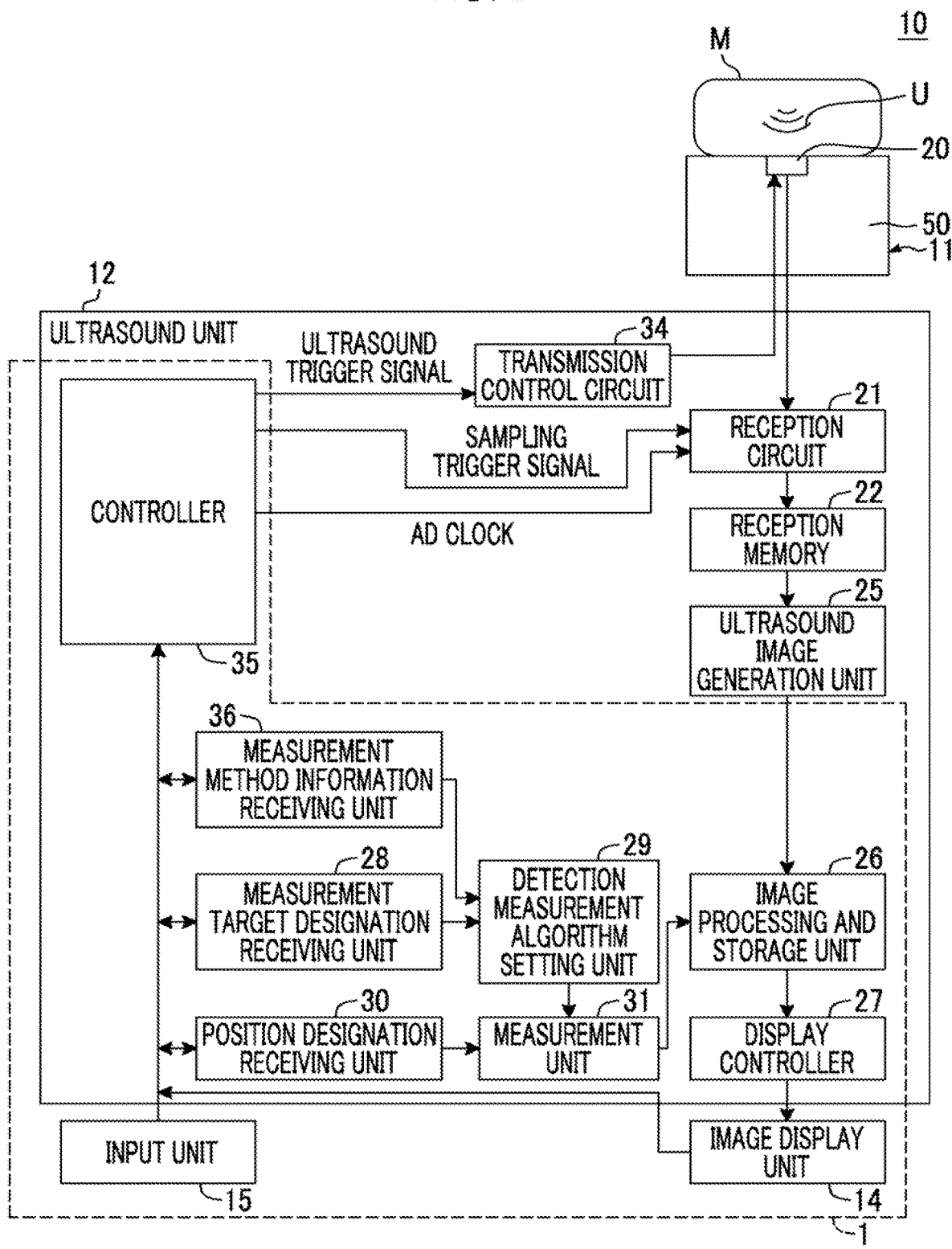
FIG. 2 is a schematic diagram showing the overall configuration of the acoustic wave image capturing apparatus shown in FIG. 1.
Figure 3:
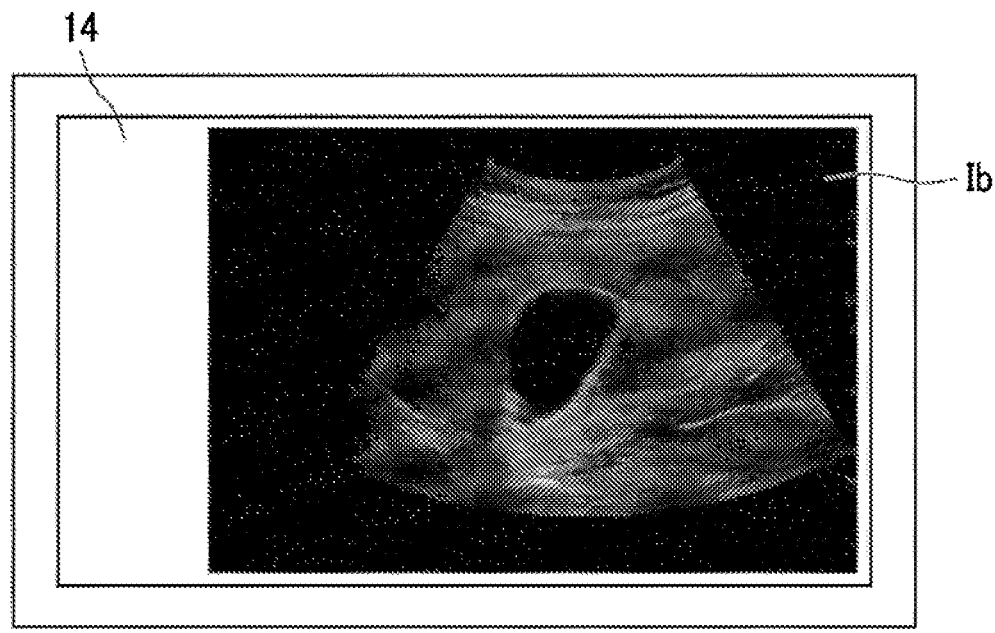
FIG. 3 is a diagram showing an example of display of an ultrasound image.
Figure 4:
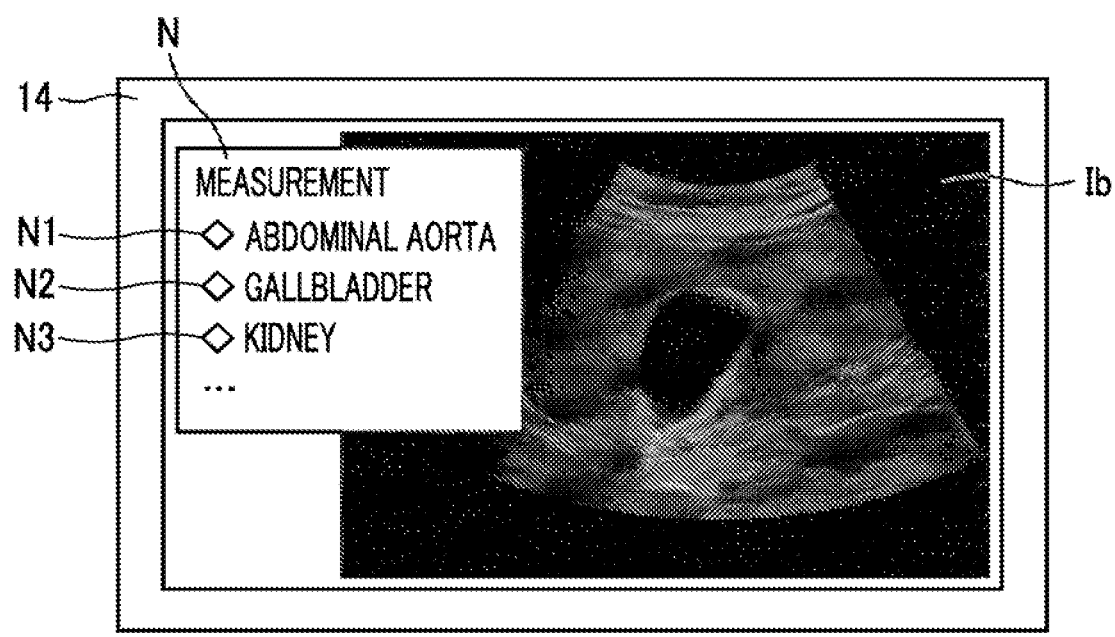
FIG. 4 is a diagram showing an example of display of a list of measurement items on an ultrasound image.
Figure 5:
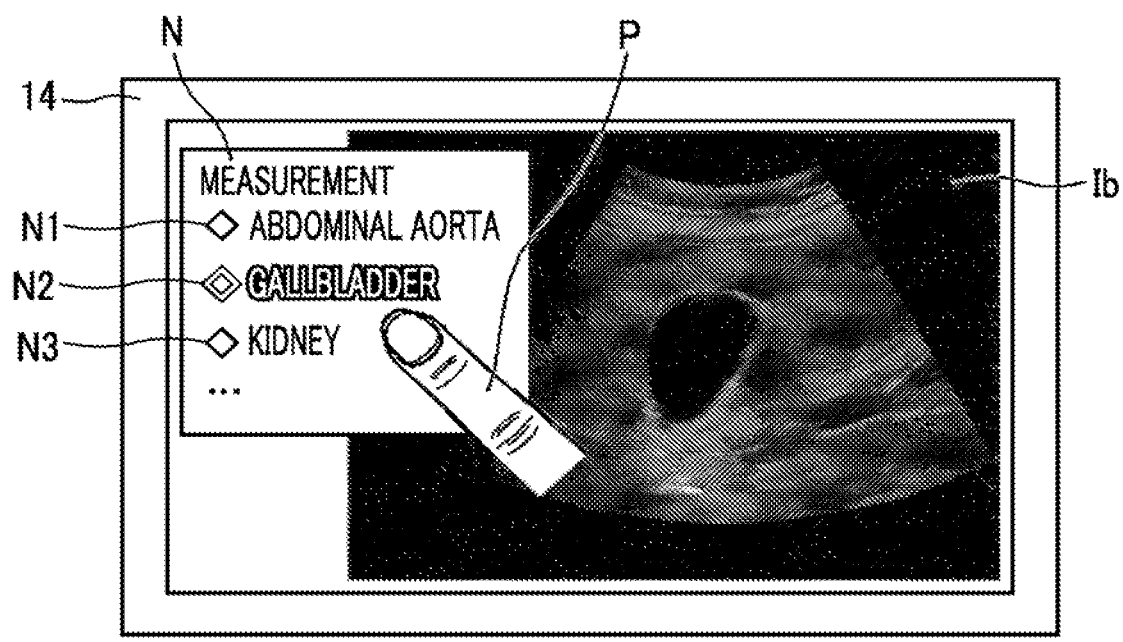
FIG. 5 is a diagram showing an example of selection in the list of measurement items displayed on an ultrasound image.
Figure 6:
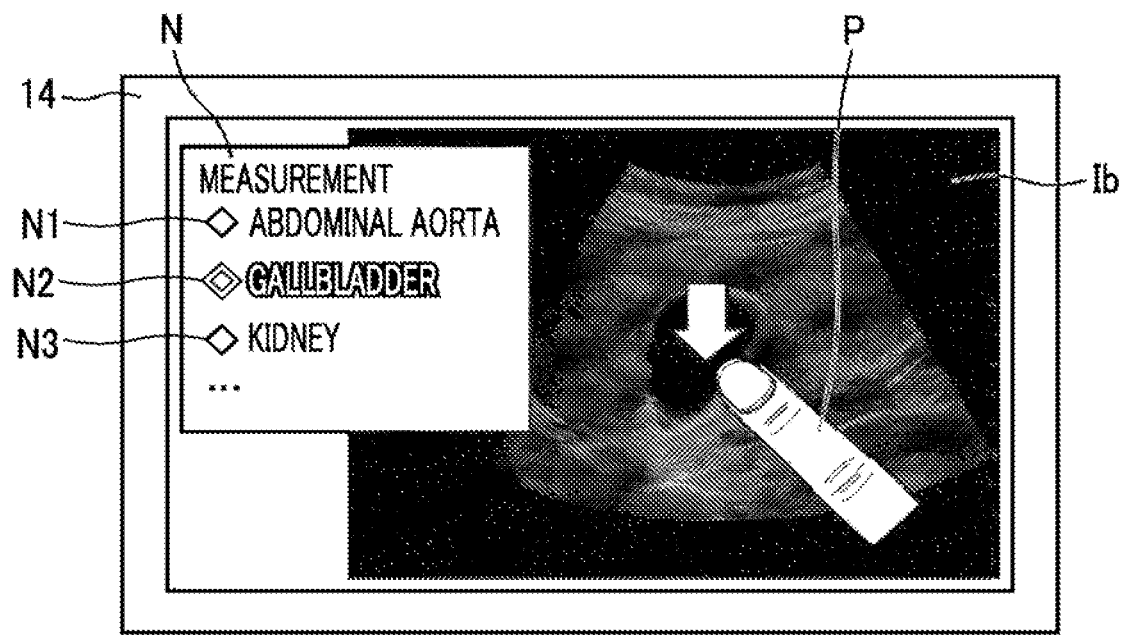
FIG. 6 is a diagram showing an example of designation of a position on an ultrasound image.
Figure 7:
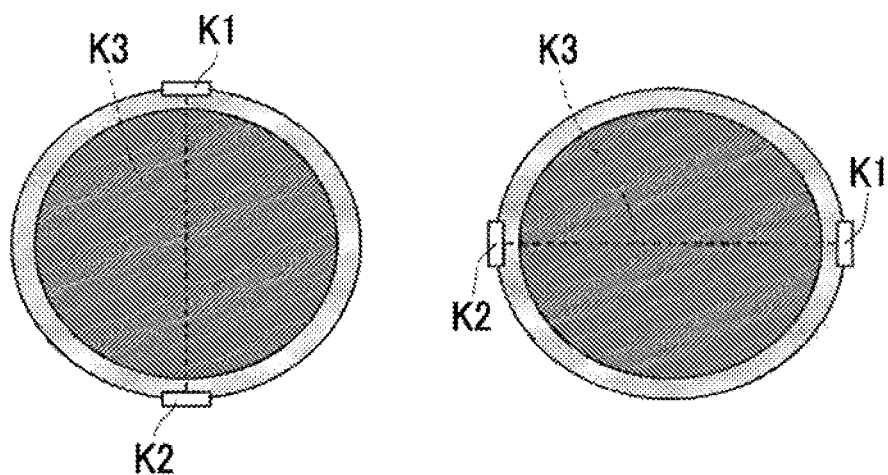
FIG. 7 is a diagram illustrating different measurement methods (part 1).
Figure 8:
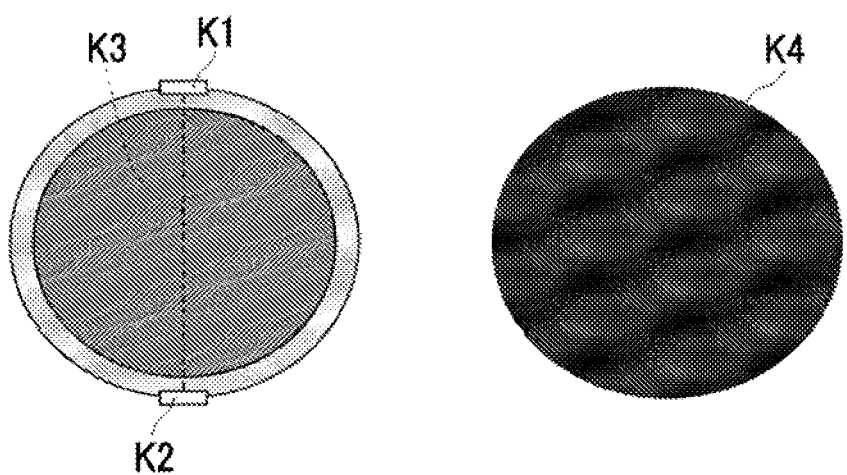
FIG. 8 is a diagram illustrating different measurement methods (part 2).
Figure 9:
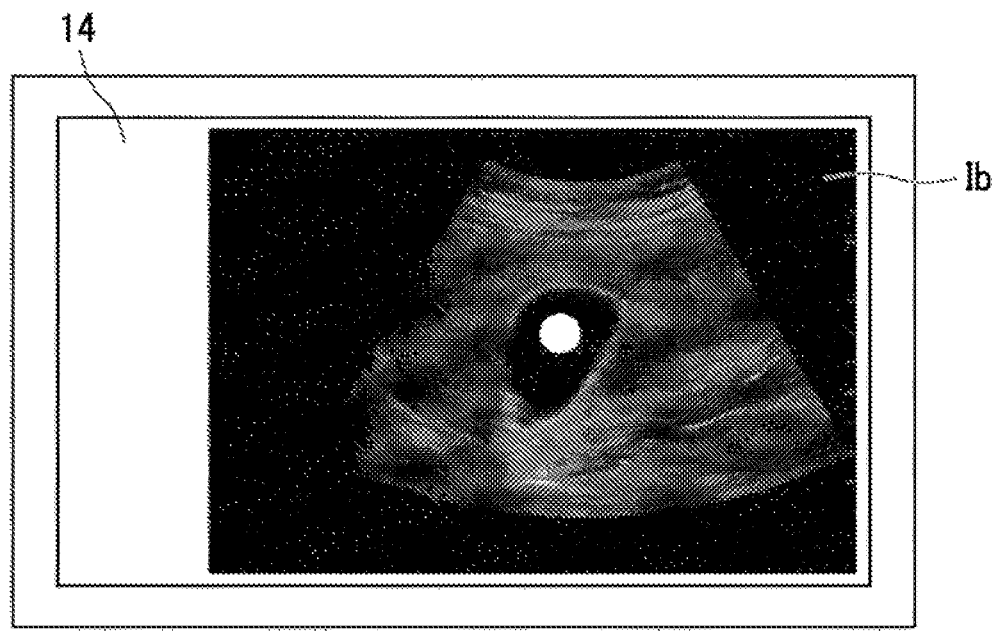
FIG. 9 is a diagram showing an example of point input on an ultrasound image.
Figure 10:
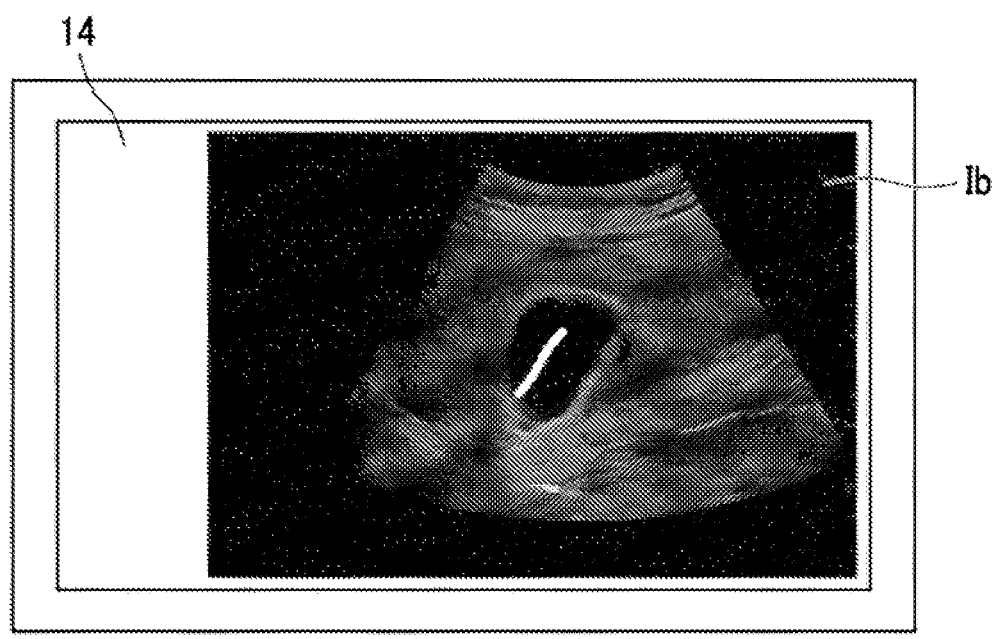
FIG. 10 is a diagram showing an example of line input on an ultrasound image.
Figure 11:
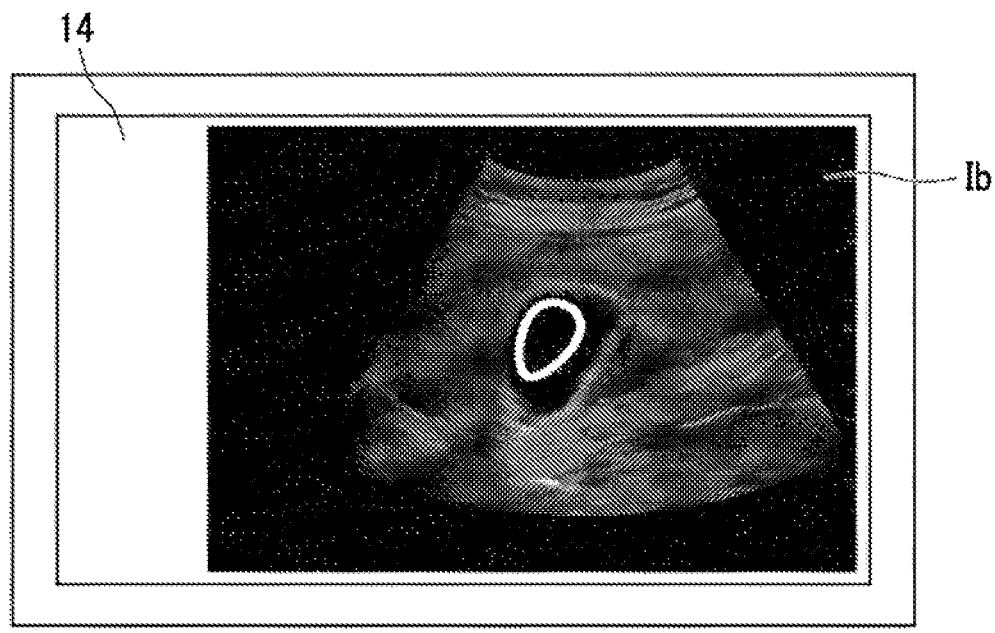
FIG. 11 is a diagram showing an example of circle input on an ultrasound image.
Figure 12:
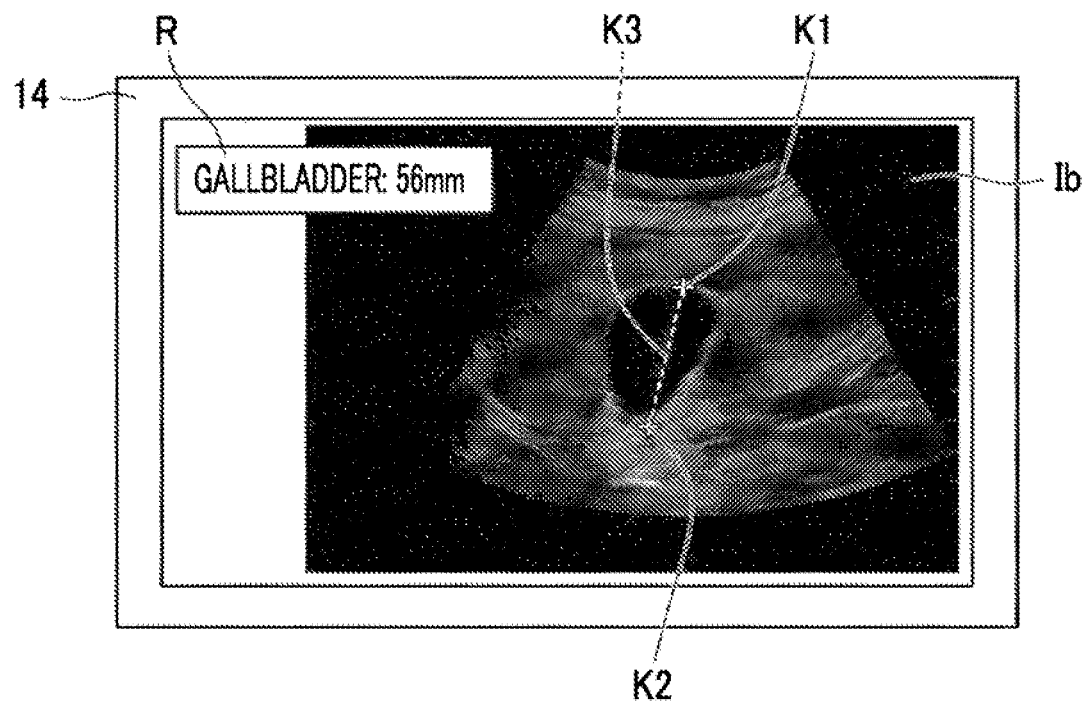
FIG. 12 is a diagram showing an example of a measurement result displayed on an ultrasound image.

Hereinafter, an acoustic wave image capturing apparatus 10 comprising an acoustic wave measurement apparatus 1 according to a first embodiment of the present invention will be described in detail with reference to the diagrams. FIG. 1 is a perspective view showing the acoustic wave image capturing apparatus 10 comprising the acoustic wave measurement apparatus 1 according to the first embodiment of the present invention. FIG. 2 is a schematic diagram showing the overall configuration of the acoustic wave image capturing apparatus 10 shown in FIG. 1. FIG. 3 is a diagram showing an example of the display of an ultrasound image Ib. FIG. 4 is a diagram showing an example of the display of a list N of measurement targets on the ultrasound image Ib. FIG. 5 is a diagram showing an example of selection in the list N of measurement targets displayed on the ultrasound image Ib. FIG. 6 is a diagram showing an example of designation of a position on the ultrasound image Ib. FIGS. 7 and 8 are diagrams illustrating different measurement methods. FIG. 9 is a diagram showing an example of point input on an ultrasound image. FIG. 10 is a diagram showing an example of line input on an ultrasound image. FIG. 11 is a diagram showing an example of circle input on an ultrasound image. FIG. 12 is a diagram showing an example of a measurement result R displayed on the ultrasound image Ib.

As an example, the acoustic wave image capturing apparatus 10 according to the present embodiment has only a function of generating an ultrasound image based on a reflected ultrasound wave detection signal. The acoustic wave measurement apparatus according to the embodiment of the present invention may be mounted in an apparatus having only a function of generating a photoacoustic image based on a photoacoustic signal, or may be mounted in an apparatus having both a function of generating a photoacoustic image and a function of generating an ultrasound image. The acoustic wave measurement apparatus according to the embodiment of the present invention can be mounted in any apparatus that can receive or store image data of at least one of a photoacoustic image or an ultrasound image of a two-dimensional image and display the received or stored image data even though the apparatus does not have any of the above-described functions.

As an example, the acoustic wave image capturing apparatus 10 is configured as a so-called portable notebook computer type apparatus, as shown in FIG. 1. Although the acoustic wave image capturing apparatus 10 of the present embodiment is of a notebook computer type, the present invention is not limited thereto, and may be of a tablet type or the like. As shown in FIGS. 1 and 2, the acoustic wave image capturing apparatus 10 comprises a probe 11 that is an ultrasound probe, an ultrasound unit 12, an image display unit 14, and an input unit 15. The ultrasound unit 12 is housed in the housing of FIG. 1. More specifically, the image display unit 14 is an image display screen including, for example, a liquid crystal display device, and is configured by a touch panel to which direct input can be performed by the operator. The image display unit 14 of the present embodiment also functions as the input unit 15. Each of the image display unit 14 and the input unit 15 is configured to be able to display a color image. Hereinafter, the components of the acoustic wave image capturing apparatus 10 will be sequentially described.

The probe 11 has a function of emitting measurement light and ultrasound waves toward the subject M that is a living body, for example. In FIG. 2, the shape of the probe 11 is schematically shown. The probe 11 has a function of detecting the acoustic wave U propagating through the subject M. The probe 11 emits (transmits) ultrasound waves (acoustic waves) to the subject M, and detects (receives) reflected ultrasound waves (reflected acoustic waves) that are returned by reflection from the subject M.

In this specification, the "acoustic wave" includes an ultrasound wave or a photoacoustic wave, and the "ultrasound wave" means an elastic wave transmitted by the probe and its reflected wave (reflected ultrasound wave). The acoustic wave emitted from the probe 11 is not limited to the ultrasound wave, and an acoustic wave having an audible frequency may be used as long as an appropriate frequency can be selected according to an examination target, measurement conditions, and the like.

The probe 11 is configured as, for example, a sector scanning probe, a linear scanning probe, or a convex scanning probe. The type of probe used for acquisition of an acoustic wave image is appropriately selected according to an imaging part and the like. The probe 11 has a transducer array 20 that is an acoustic wave detector, and the transducer array 20 is housed in a housing 50. In the present embodiment, the transducer array 20 also functions as an ultrasound wave transmission element. The transducer array 20 is connected to a circuit for transmitting ultrasound waves, a circuit for receiving acoustic waves, and the like through wiring lines (not shown).

The transducer array 20 has a plurality of ultrasound transducers arranged in one direction. The ultrasound transducer is an electroacoustic transducer. The ultrasound transducer is a piezoelectric element formed of, for example, piezoelectric ceramics. Alternatively, the ultrasound transducer may be a piezoelectric element formed of a polymer film, such as polyvinylidene difluoride (PVDF). The ultrasound transducer converts the received acoustic wave U into an electrical signal.

Although an example of the transducer array 20 in which a plurality of ultrasound transducers are arranged in a one-dimensional manner has been described above, the transducer array 20 is not limited thereto. In the transducer array 20, a plurality of ultrasound transducers may be arranged in a two-dimensional manner.

In the transducer array 20, in a case where an alternating voltage is applied to the ultrasound transducer, the ultrasound transducer generates an ultrasound wave having a frequency corresponding to the frequency of the alternating voltage, and the ultrasound wave is transmitted from the transducer array 20. In addition, transmission and reception of ultrasound waves may be separated from each other. That is, for example, ultrasound waves may be transmitted from a position different from the probe 11, and reflected ultrasound waves of the transmitted ultrasound waves may be received by the probe 11.

The ultrasound unit 12 has a reception circuit 21, a reception memory 22, an ultrasound image generation unit 25, an image processing and storage unit 26, a display control unit 27, a measurement target designation receiving unit 28, a detection measurement algorithm setting unit 29, a position designation receiving unit 30, a measurement unit 31, a transmission control circuit 34, a control unit 35, and a measurement method information receiving unit 36. In the present embodiment, the acoustic wave measurement apparatus 1 that is an embodiment of the present invention is configured by the image display unit 14, the input unit 15, the image processing and storage unit 26, the display control unit 27, the measurement target designation receiving unit 28, the detection measurement algorithm setting unit 29, the position designation receiving unit 30, the measurement unit 31, the control unit 35, and the measurement method information receiving unit 36. The ultrasound unit 12 typically has a processor, a memory, a bus, and the like. Programs relevant to ultrasound image generation processing and the like are installed on the memory of the ultrasound unit 12. The configuration of the hardware of the ultrasound unit 12 is not particularly limited, and can be realized by appropriately combining a plurality of integrated circuits (ICs), processors, application specific integrated circuits (ASICs), field-programmable gate arrays (FPGAs), memories, and the like.

The control unit 35 controls each unit of the acoustic wave measurement apparatus 1, and controls each unit of the acoustic wave image capturing apparatus 10. For example, by operating a program using the control unit 35 configured by a processor, the functions of the reception circuit 21, the ultrasound image generation unit 25, the image processing and storage unit 26, the display control unit 27, the measurement target designation receiving unit 28, the detection measurement algorithm setting unit 29, the position designation receiving unit 30, the measurement unit 31, the transmission control circuit 34, the measurement method information receiving unit 36, and the like are realized. That is, each of these units is formed by the memory on which the programs are installed and the processor. In the case of acquiring an ultrasound image, the control unit 35 transmits an ultrasound trigger signal for instructing the transmission control circuit 34 to transmit ultrasound waves. In a case where the ultrasound trigger signal is received, the transmission control circuit 34 causes the probe 11 to transmit ultrasound waves. The control unit 35 transmits a sampling trigger signal to the reception circuit 21 according to the timing of ultrasound wave transmission, thereby starting the sampling of the reflected ultrasound wave signal.

The reception circuit 21 receives the reflected ultrasound wave detection signal output from the transducer array 20 of the probe 11, and stores the received detection signal in the reception memory 22. Typically, the reception circuit 21 is configured to include a low noise amplifier, a variable gain amplifier, a low pass filter, and an AD converter. The reflected ultrasound wave detection signal output from the probe 11 is amplified by the low noise amplifier and then the gain is adjusted according to the depth by the variable gain amplifier, and high frequency components are cut by the low pass filter and then conversion into a digital signal is performed by the AD converter and the digital signal is stored in the reception memory 22. The reception circuit 21 is configured by, for example, one integrated circuit (IC). The above-described low pass filter is provided to prevent aliasing noise from occurring at the time of AD conversion. The cut-off frequency of the low pass filter is generally set to a frequency that is about half the sampling frequency of AD conversion. Specifically, the cut-off frequency of the low pass filter is set to about 10 MHz to 30 MHz.

A digitized reflected ultrasound wave detection signal is stored in the reception memory 22. More specifically, the reflected ultrasound wave detection signal is a signal obtained by detecting a reflected acoustic wave that is a reflected wave of an ultrasound wave, which is an acoustic wave emitted toward the subject M, in the subject M.

The ultrasound image generation unit 25 generates an ultrasound image (tomographic image) by reconstructing the reflected ultrasound wave detection signal received from the reception memory 22. Specifically, the ultrasound image generation unit 25 adds a reflected ultrasound wave detection signal based on a signal output from each ultrasound transducer with a delay time corresponding to the position of each ultrasound transducer of the transducer array 20, thereby generating a reflected ultrasound wave detection signal for one line (delay addition method). The ultrasound image generation unit 25 may perform reconstruction using a circular back projection (CBP) method instead of the delay addition method. Alternatively, the ultrasound image generation unit 25 may perform reconstruction using a Hough transform method or a Fourier transform method. The reconstructed reflected ultrasound wave detection signals for a plurality of lines are subjected to signal processing, such as detection processing and logarithmic conversion processing, and then are transmitted to the display control unit 27 through the image processing and storage unit 26 as signals for displaying an ultrasound image (tomographic image) regarding a cross section of the subject M.

The image processing and storage unit 26 performs various kinds of processing for image quality improvement, such as brightness correction, gradation correction, sharpness correction, and color correction, on the image data of the ultrasound image. The image processing and storage unit 26 of the present embodiment also functions as a storage unit that stores various databases and a storage unit that stores, as image data, a signal for displaying the image generated by the ultrasound image generation unit 25. Although the image processing and storage unit 26 of the acoustic wave measurement apparatus 1 and the acoustic wave image capturing apparatus 10 of the present embodiment comprises both an image processing function and a function as a storage unit, the acoustic wave measurement apparatus according to the embodiment of the present invention may have only a function as a storage unit without having an image processing function.

The display control unit 27 displays the ultrasound image Ib on the image display unit 14 as shown in FIG. 3 based on the above-described signal for displaying the ultrasound image.

The measurement target designation receiving unit 28 receives designation of a measurement target. Specifically, in a case where the measurement function is started on a user interface (UI) application by the operator, the list N of measurement targets is displayed on the image display unit 14 as shown in FIG. 4. For each measurement target displayed in the list N of measurement targets, the name of the organ is described. For example, abdominal aorta N1, gallbladder N2, and kidney N3, and the like are displayed. Although only the name of the organ is displayed as the measurement target in the present embodiment, the present invention is not limited thereto. Without being limited to the name of the organ, only items relevant to the names or abnormalities of lesions such as tumors, cysts, and bleeding may be displayed, or the display content can be appropriately changed.

In a case where the list N of measurement targets is displayed on the image display unit 14 as shown in FIG. 4, the operator selects, for example, the gallbladder N2 as a desired measurement target from the list N of measurement targets using a finger P as shown in FIG. 5, and the measurement target designation receiving unit 28 receives the gallbladder N2 selected by the operator as a measurement target. The measurement target designation receiving unit 28 assigns a recognition number, that is, an identification (ID) to each received measurement target. Although the measurement target designation receiving unit 28 of the present embodiment receives a selection item selected by a touch panel, the present invention is not limited thereto. For example, an input device, such as a mouse, a track pad, or a track ball, may be used as an input unit, and a selection item selected by the input unit may be received.

The position designation receiving unit 30 receives designation of the position of a measurement target on the ultrasound image Ib displayed on the image display unit 14. Specifically, in a case where the measurement item received by the measurement target designation receiving unit 28 is the gallbladder N2, the operator desires to measure the gallbladder. Therefore, the measurement target is the gallbladder. Then, as shown in FIG. 6, the operator designates a position where the operator himself or herself thinks that the gallbladder is present on the ultrasound image Ib, for example, the tip of the arrow in FIG. 6 using the finger P. The position designation receiving unit 30 receives the position designated by the operator as a measurement target position.

The measurement method information receiving unit 36 receives measurement method information indicating a measurement method. In general, in the case of measuring the diameters of various organs, for example, the measurement method may differ depending on the operator, such as a facility or an examining person. For example, there are a case of measuring the diameter (line K3) in the vertical direction as shown in the left diagram of FIG. 7 and a case of measuring the diameter (line K3) in the horizontal direction as shown in the right diagram of FIG. 7. Even for the same organ, different items may be measured. For example, there are a case of measuring the diameter (line K3) as shown in the left diagram of FIG. 8 and a case of measuring the area (region K4) as shown in the right diagram of FIG. 8. Thus, there are a plurality of measurement methods for one organ.

Then, the measurement method information receiving unit 36 receives the movement of the finger P of the operator on the ultrasound image Ib displayed on the image display unit 14 as coordinate information, and determines a measurement method desired by the operator based on the received coordinate information. Specifically, as shown in FIG. 9, in a case where the operator inputs a point with the finger P at a position where the operator himself or herself thinks that the gallbladder is present on the ultrasound image Ib, the coordinates specified with the finger P are coordinates where the start point (x1, y1) and the end point (x2, y2) are equal. Therefore, the measurement method information receiving unit 36 determines that one point has been input.

In addition, as shown in FIG. 10, in a case where the operator inputs a line with the finger P at a position where the operator himself or herself thinks that the gallbladder is present on the ultrasound image Ib, the coordinates input with the finger P are coordinates where the start point (x1, y1) and the end point (xn, yn) are different. Therefore, since the point (x2, 2) to the point (x(n−1), y(n−1)) are present in a straight line, the measurement method information receiving unit 36 determines that a straight line has been input.

In addition, as shown in FIG. 11, in a case where the operator inputs a circle with the finger P at a position where the operator himself or herself thinks that the gallbladder is present on the ultrasound image Ib, the coordinates input with the finger P are coordinates where the start point (x1, y1) and the end point (xn, yn) are equal. Therefore, since the point (x2, 2) to the point (x(n−1), y(n−1)) are present in a non-linear shape, the measurement method information receiving unit 36 determines that a closed loop has been input.

In addition, although not shown, in a case where the operator inputs a curve with the finger P at a position where the operator himself or herself thinks that the gallbladder is present on the ultrasound image Ib, the coordinates input with the finger P are coordinates where the start point (x1, y1) and the end point (x2, y2) are different. Therefore, since the point (x2, 2) to the point (x(n−1), y(n−1)) are present in a non-linear shape, the measurement method information receiving unit 36 determines that a curve has been input.

By calculating vector information (r, θ) from a plurality of pieces of coordinate information based on the movement of the finger P of the operator, the direction of the straight line input by the operator, such as a vertical direction, a horizontal direction, and a right diagonal direction, is calculated. The area may be calculated from the plurality of pieces of coordinate information, or the movement speed of the finger P may be calculated by detecting the movement time and distance of the coordinates. In the case of calculating the area, at the time of performing processing for detecting a measurement target M1 while changing the scale in a region of interest (ROI) in the detection measurement algorithm setting unit 29 to be described later, the reference scale of the ROI can be set based on the calculated area. For example, it is possible to improve both the detection accuracy and the processing speed by performing the detection processing by finely changing the ROI scale around the position designated by the operator. In the case of calculating the speed, the detection measurement algorithm setting unit 29 to be described later can perform switching between algorithms with different accuracy, that is, different calculation amounts, according to the speed. For example, in a case where the movement of the finger P is relatively slow, it is assumed that the operator desires to perform measurement carefully and precisely without worrying about time. Accordingly, detection and measurement are performed with accuracy priority while finely changing parameters, or an advanced algorithm, for example, pattern matching that requires longer calculation time than histogram analysis but has higher accuracy than the histogram analysis is automatically selected. Conversely, in a case where the movement of the finger P is relatively fast, it is assumed that the operator desires to know the measurement result quickly. Accordingly, detection and measurement are performed with speed priority while roughly changing parameters, or a light algorithm, for example, histogram analysis that has lower accuracy than pattern matching but requires a shorter calculation time is automatically selected.

The measurement method information receiving unit 36 assigns a recognition number, that is, an ID as measurement method information indicating the measurement method, based on the information of the movement of the finger P of the operator. For example, ID1 is assigned in a case where it is determined that a point has been input, ID2 is assigned in a case where it is determined that a straight line in the horizontal direction has been input, and ID3 is assigned in a case where it is determined that a straight line in the right diagonal direction has been input. In a case where the measurement method information receiving unit 36 determines ID1, that is, determines that a point has been input, it is determined that there is no measurement method desired by the operator, and a default measurement method set in advance at the input position is adopted.

In the present embodiment, the operator moves the finger P on the measurement target on the ultrasound image Ib, the present invention is not limited thereto. In a case where the position designation receiving unit 30 receives designation of the position of the measurement target on the ultrasound image Ib in advance, the finger P may be moved in a region other than the measurement target on the screen of the image display unit 14. For example, in a case where the measurement target is a relatively small region, the movement of the finger P is small. Therefore, it is difficult to acquire the movement of the finger P, that is, measurement method information. On the other hand, by moving the finger P in a region other than the measurement target, the restriction on the movement amount of the finger P is reduced. Therefore, the movement of the finger P, that is, measurement method information can be easily obtained. In this case, in a case where the position designation receiving unit 30 receives the designation of the position of the measurement target on the ultrasound image Ib, a region having a preset size including the designated position may be displayed in an enlarged manner on the image display unit 14, so that the finger P is moved on the region displayed in an enlarged manner. In this manner, it is possible to increase the movement amount of the finger P on the measurement target. For example, in a case where both a touch panel and a track pad are provided as the input unit 15, the designation of the position of the measurement target in the position designation receiving unit 30 may be performed by the touch panel, and the input of measurement method information may be performed by the track pad.

In the present embodiment, the reception of the designation of the position of the measurement target by the position designation receiving unit 30 and the reception the designation of the measurement method information by the measurement method information receiving unit 36 are performed as separate operations by the operator. That is, the reception of the designation of the position of the measurement target by the position designation receiving unit 30 and the reception of the measurement method information by the measurement method information receiving unit 36 are received separately. However, the present invention is not limited to this, and the reception of the designation of the position of the measurement target by the position designation receiving unit 30 and the reception of the measurement method information by the measurement method information receiving unit 36 may be performed as a series of operations. That is, the reception of the designation of the position of the measurement target by the position designation receiving unit 30 and the reception of the measurement method information by the measurement method information receiving unit 36 may be received integrally. In this case, the measurement method information receiving unit 36 can be made to have the function of the position designation receiving unit 30.

The detection measurement algorithm setting unit 29 sets IDs of a detection algorithm and a measurement algorithm based on the ID of the measurement target received by the measurement target designation receiving unit 28 and the ID of measurement method information indicating the measurement method received by the measurement method information receiving unit 36. In general, the algorithm for detecting a measurement target on an image differs depending on the type of organ, lesion, or the like. In addition, the algorithm for measuring a measurement target on the image also differs depending on the measurement content, such as measuring the diameter, measuring the size, or measuring the length. The detection measurement algorithm setting unit 29 stores IDs of an algorithm corresponding to each measurement target and an algorithm corresponding to each measurement content as an association table, and sets the ID of the detection measurement algorithm with reference to the above-described association table in a case where the measurement target designation receiving unit 28 receives a measurement target and the measurement method information receiving unit 36 receives measurement method information. For example, in a case where the aorta (ID1) is received as a measurement target and information indicating that ID2, that is, a straight line in the horizontal direction is input as measurement method information, the detection measurement algorithm sets the ID2 indicating the horizontal measurement of the aorta. Here, in a case where there is only one measurement method capable of measuring the measurement target received by the measurement target designation receiving unit 28, the detection measurement algorithm setting unit 29 neglects the measurement method information received by the measurement method information receiving unit 36 and sets a detection measurement algorithm based on the measurement method capable of measuring the measurement target. As the detection measurement algorithm, a known algorithm that is generally used can be used. The algorithm referred to herein defines a procedure (calculation procedure) for achieving a certain purpose (detection or measurement). For example, the algorithm referred to herein is implemented as a software program in an apparatus and is executed by a processor.

For example, for a measurement target detection algorithm, there is a method in which typical pattern data is stored in advance as a template, a pattern data similarity is calculated while searching for an image with a template, and it is considered that a target is present in a place where the similarity is equal to or greater than a predetermined threshold value and is the maximum. For the calculation of the similarity, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012) can be used.

In a case where the designation of the position of the measurement target is received by the position designation receiving unit 30, The measurement unit 31 detects the measurement target based on the position of the measurement target received by the position designation receiving unit 30 and the detection measurement algorithm set by the detection measurement algorithm setting unit 29, and performs measurement for the detected measurement target. The measurement unit 31 determines the position of a detection range for detecting the measurement target based on the received position, and detects the inside of the detection range at the determined position. The size of the detection range is set in the measurement unit 31 in advance, but can be changed by the operator.

Specifically, in a case where the measurement item received by the measurement target designation receiving unit 28 is the gallbladder N2, the measurement unit 31 first detects the gallbladder on the ultrasound image Ib within the detection range based on the detection algorithm set by the detection measurement algorithm setting unit 29. The measurement unit 31 detects the accurate position and region of the gallbladder on the ultrasound image Ib. Then, the measurement unit 31 determines an optimal measurement point for the detected gallbladder based on the measurement algorithm set by the detection measurement algorithm setting unit 29. Specifically, as shown in FIG. 12, the measurement unit 31 determines two longest distance points on the boundary surrounding the gallbladder region on the ultrasound image Ib as measurement points K1 and K2, and measures the length of a line K3 connecting the measurement points K1 and K2 to each other. In FIG. 12, the length of the line K3 is 56 mm. The measurement unit 31 displays the measurement points K1 and K2 and the line K3 and the measurement target and the length as a measurement result R, that is, gallbladder: 56 mm, on the image display unit 14 through the image processing and storage unit 26 and the display control unit 27.

In the present embodiment, the measurement unit 31 determines the position of the detection range for detecting the measurement target based on the position received by the position designation receiving unit 30. However, the present invention is not limited thereto, and the measurement unit 31 may further determine the measurement position for measuring the measurement target, that is, the positions of the measurement points K1 and K2. For example, in a case where the measurement target is a long blood vessel or the like, which diameter is to be measured is determined based on the received position. For example, the shortest line passing through the received position can be determined as the line K3, and points at both ends of the line K3 can be determined as the measurement points K1 and K2.

In a case where the detection range for detecting the measurement target is the entire ultrasound image Ib, the measurement unit 31 does not need to determine the position of the range for detecting the measurement target. For this reason, the measurement unit 31 may determine the measurement position for measuring the measurement target, that is, only the positions of the measurement points K1 and K2.

Figure 13:
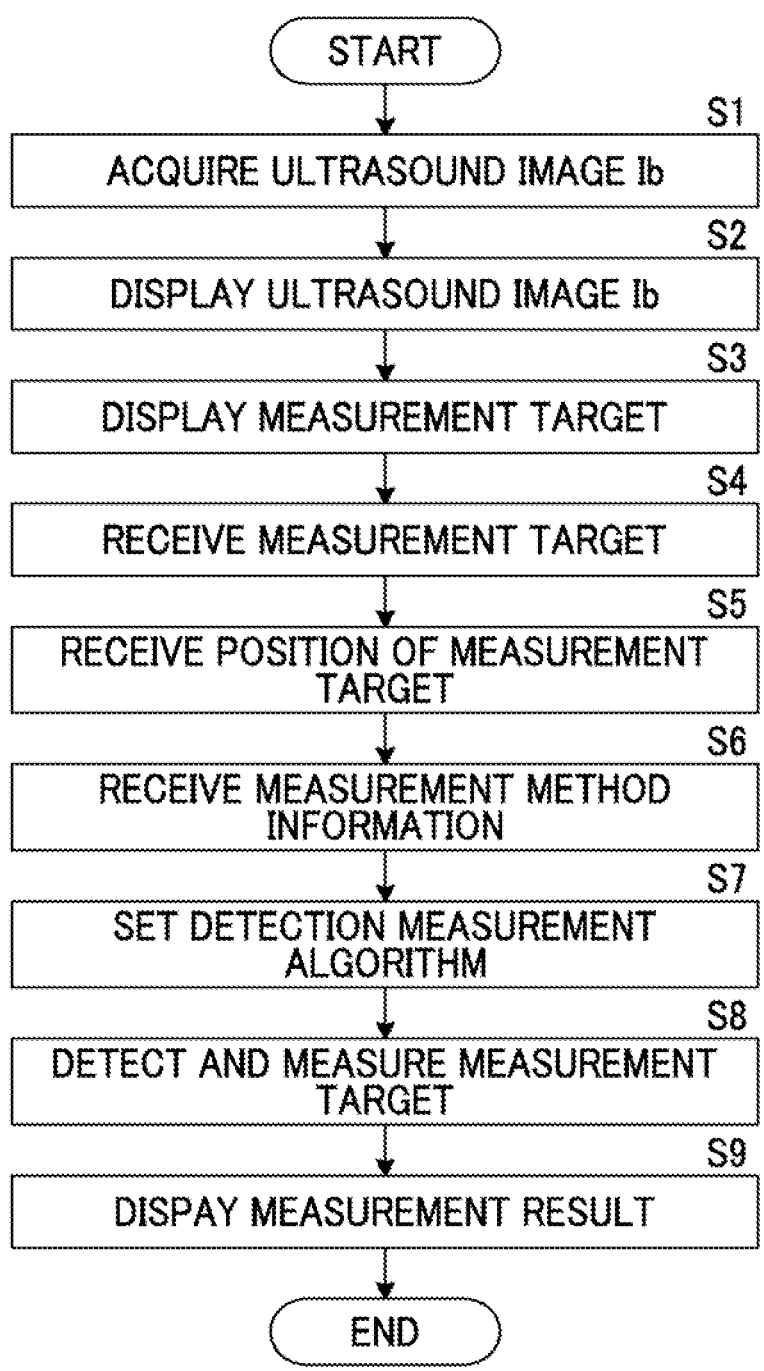
FIG. 13 is a flowchart showing a method of a series of processes of the acoustic wave measurement apparatus shown in FIG. 2.

Next, an operation method of an acoustic wave measurement apparatus, in which the acoustic wave measurement apparatus 1 measures a measurement target in the ultrasound image Ib displayed on the image display unit 14, in the acoustic wave image capturing apparatus 10 described above will be described. FIG. 13 is a flowchart showing a method of a series of processes of the acoustic wave measurement apparatus 1 shown in FIG. 2.

As shown in FIG. 8, in the acoustic wave measurement apparatus 1, the image processing and storage unit 26 receives and stores image data of the ultrasound image Ib generated by the ultrasound image generation unit 25, thereby acquiring the ultrasound image Ib (step S1). In the present embodiment, the image processing and storage unit 26 receives and stores the image data of the ultrasound image Ib generated by the ultrasound image generation unit 25, thereby acquiring the ultrasound image Ib. However, the present invention is not limited thereto, and the ultrasound image Ib may be acquired by inputting the image data of the ultrasound image Ib, which is stored in external storage means in advance, through an input and output unit (not shown) provided in the acoustic wave measurement apparatus 1. The present invention can also be applied to a case where the image data of the ultrasound image Ib generated by the ultrasound image generation unit 25 is displayed on the image display unit 14 by the display control unit 27 without being temporarily stored in the image processing and storage unit 26.

Then, the display control unit 27 displays the image data of the ultrasound image Ib, which is stored in the image processing and storage unit 26 and has been subjected to various kinds of image processing, on the image display unit 14 (step S2). In a case where the measurement function is started by the operator on the UI application, the display control unit 27 displays the list N of measurement targets on the image display unit 14 as shown in FIG. 4 (step S3).

In a case where the list N of measurement targets is displayed on the image display unit 14, the operator designates the gallbladder N2 as a desired measurement target from the list N of measurement targets using the finger P as shown in FIG. 5, and the measurement target designation receiving unit 28 receives the gallbladder N2 selected by the operator as a measurement target (step S4).

Then, the position designation receiving unit 30 receives designation of the position of the measurement target, that is, the gallbladder on the ultrasound image Ib displayed on the image display unit 14 (step S5), and the measurement method information receiving unit 36 receives measurement method information, here, an input of the straight line in the vertical direction as described above (step S6). Then, the detection measurement algorithm setting unit 29 sets a detection measurement algorithm for the size of the gallbladder in the vertical direction (step S7).

Then, the measurement unit 31 detects the inside of the detection range based on the detection algorithm set by the detection measurement algorithm setting unit 29, and detects the accurate position and region of the gallbladder on the ultrasound image Ib. The measurement unit 31 determines the optimal measurement points K1 and K2 for the detected gallbladder, and measures the length of the line K3 connecting the measurement points K1 and K2 to each other (step S8). Then, the measurement unit 31 displays the measurement points K1 and K2 and the line K3 and the measurement target and the length as the measurement result R, that is, gallbladder: 56 mm, on the image display unit 14 through the image processing and storage unit 26 and the display control unit 27 (step S9). As described above, the acoustic wave measurement apparatus 1 measures the measurement target.

According to the acoustic wave measurement apparatus 1 and the operation method of the acoustic wave measurement apparatus 1 of the present embodiment, in a case where the operator designates the approximate position of the measurement target M1 on the acoustic wave image displayed on the image display unit 14 and inputs information indicating a measurement method such as a measurement direction, for example, inputs a straight line in the vertical direction or inputs a straight line in the horizontal direction, the measurement unit can automatically detect and measure a measurement target. In this manner, by reducing the measurement method selection work or the measurement result selection work of the operator, it is possible to measure the measurement target quickly and easily with less effort and perform measurement with reduced variations by the operator.

Figure 14:
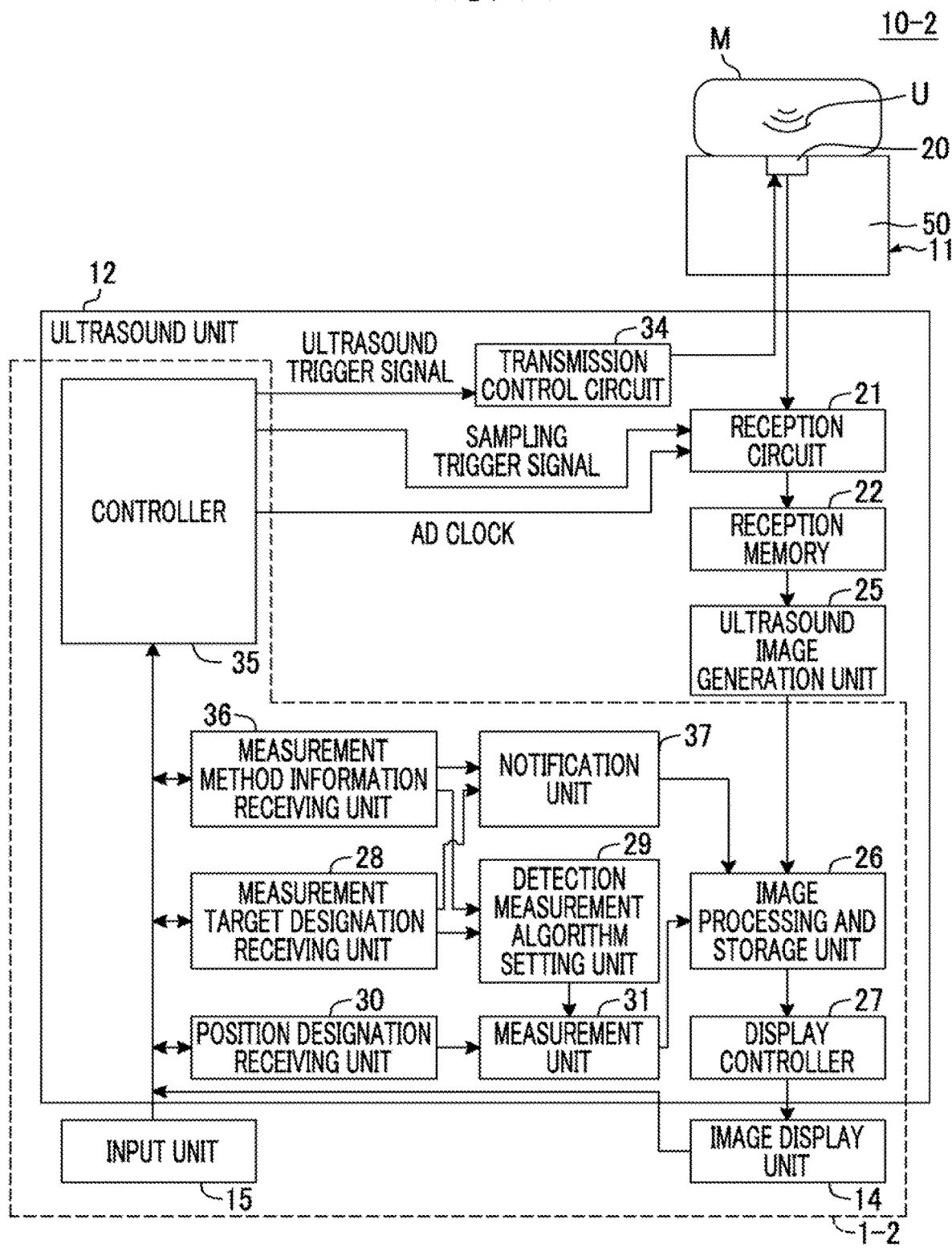
FIG. 14 is a schematic diagram showing the overall configuration of an acoustic wave image capturing apparatus comprising an acoustic wave measurement apparatus according to a second embodiment of the present invention.

Next, an acoustic wave image capturing apparatus 10-2 comprising an acoustic wave measurement apparatus 1-2 according to a second embodiment of the present invention will be described in detail with reference to the diagrams. FIG. 14 is a schematic diagram showing the overall configuration of the acoustic wave image capturing apparatus 10-2 comprising the acoustic wave measurement apparatus 1-2 according to the second embodiment of the present invention. The acoustic wave measurement apparatus 1-2 shown in FIG. 14 is obtained by further providing a notification unit 37 in the acoustic wave measurement apparatus 1 shown in FIG. 1, and the other components are the same as those of the acoustic wave measurement apparatus 1 shown in FIG. 1. Therefore, the same components are denoted by the same reference numerals for the sake of convenience, and the description thereof will be omitted herein.

The acoustic wave measurement apparatus 1-2 shown in FIG. 14 comprises the notification unit 37. In a case where there is only one measurement method by which the measurement target received by the measurement target designation receiving unit 28 can be measured, the notification unit 37 notifies the operator of information regarding the possible measurement method before measurement. Specifically, for example, in a case where there is only a measurement method in the horizontal direction, before the measurement method information receiving unit 36 receives the measurement method, the notification unit 37 causes the image display unit 14 to display a text display "This measurement target can be measured only in the horizontal direction". Alternatively, the notification unit 37 may provide notification by graphical user interface (GUI) display or may provide notification by sound using a speaker or the like (not shown), and the notification method can be appropriately changed. In a case where the notification unit 37 provides notification by GUI display, the function of the notification unit 37 is realized, for example, by causing the control unit 35 configured by a processor to operate a program and causing the image display unit 14 to display the GUI. In a case where the notification unit 37 provides notification by sound, the function of the notification unit 37 is realized, for example, by causing the control unit 35 configured by a processor to operate a program and causing a speaker or the like to output sound. Thus, by comprising the notification unit 37, it is possible to prevent the operator from inputting a wrong measurement method.

Figure 15:
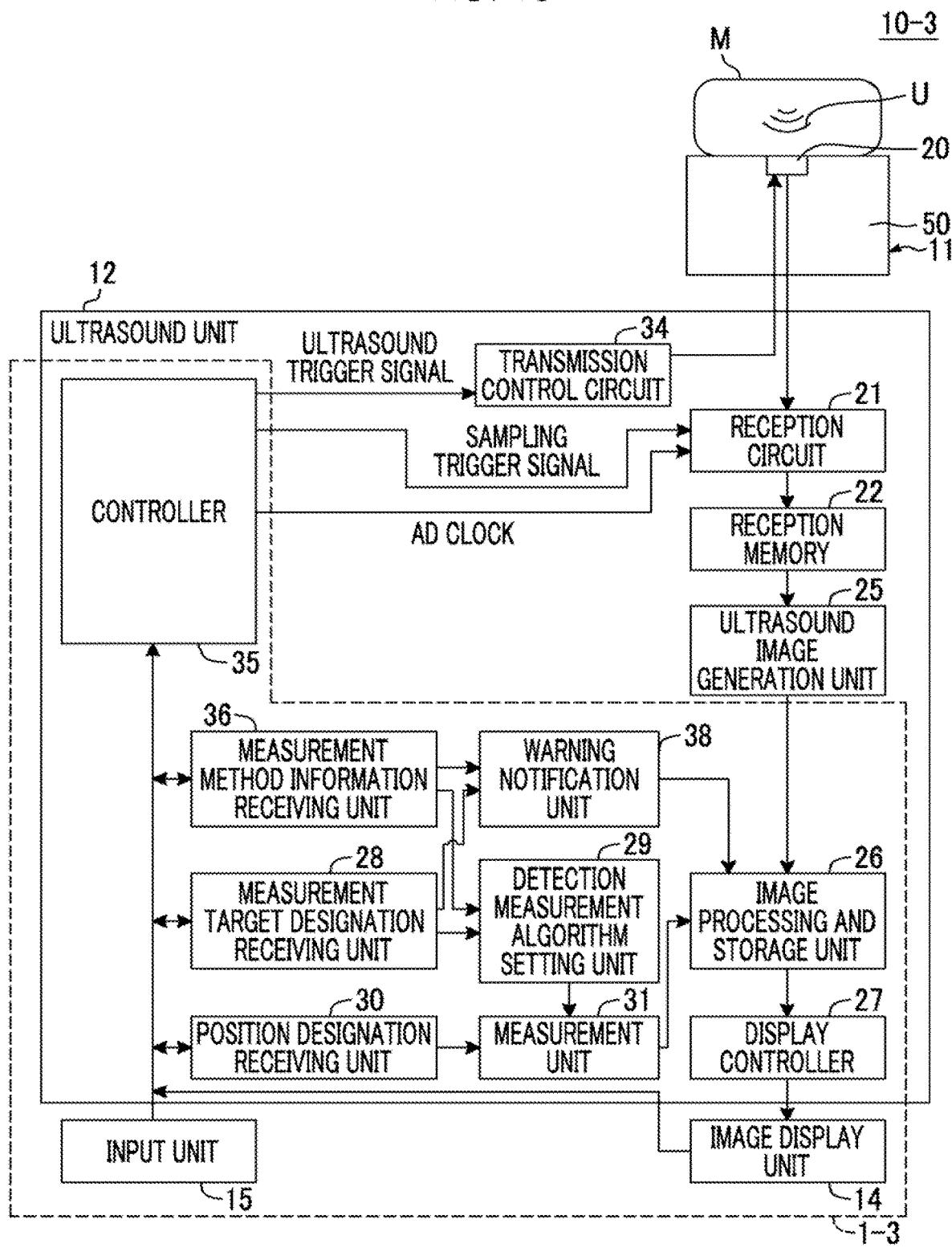
FIG. 15 is a schematic diagram showing the overall configuration of an acoustic wave image capturing apparatus comprising an acoustic wave measurement apparatus according to a third embodiment of the present invention.

Next, an acoustic wave image capturing apparatus 10-3 comprising an acoustic wave measurement apparatus 1-3 according to a third embodiment of the present invention will be described in detail with reference to the diagrams. FIG. 15 is a schematic diagram showing the overall configuration of the acoustic wave image capturing apparatus 10-3 comprising the acoustic wave measurement apparatus 1-3 according to the third embodiment of the present invention. The acoustic wave measurement apparatus 1-3 shown in FIG. 15 is obtained by further providing a warning notification unit 38 in the acoustic wave measurement apparatus 1 shown in FIG. 1, and the other components are the same as those of the acoustic wave measurement apparatus 1 shown in FIG. 1. Therefore, the same components are denoted by the same reference numerals for the sake of convenience, and the description thereof will be omitted herein.

The acoustic wave measurement apparatus 1-3 shown in FIG. 15 comprises the warning notification unit 38. The warning notification unit 38 gives a warning in a case where the detection measurement algorithm setting unit 29 cannot set a detection measurement algorithm based on the measurement method information received by the measurement method information receiving unit 36. Specifically, for example, in a case where there are two measurement methods of measurement in the vertical direction and area measurement, in a case where the measurement method information received by the measurement method information receiving unit 36 is a measurement method different from the measurement in the vertical direction and the area measurement, for example, measurement in the horizontal direction, the warning notification unit 38 causes the image display unit 14 to display a text display "This measurement target corresponds to measurement in the vertical direction and area measurement". In a case where there is only size measurement as a measurement method, that is, there is only length measurement such as a vertical direction, a horizontal direction, and a diagonal direction, in a case where the measurement method information received by the measurement method information receiving unit 36 is area measurement, the warning notification unit 38 causes the image display unit 14 to display a text display "This measurement target corresponds to only length measurement". In this case, the apparatus side does not need to recognize that the operator's input (gesture (for example, finger movement)) is measurement in the horizontal direction or search for a measurement method corresponding to the horizontal direction, and it is sufficient to be able to identify information other than the stored measurement method information for the vertical direction and the area, that is, measurement method information set in advance for the measurement target.

As described above, by providing notification of the measurement method that can be executed by the detection measurement algorithm setting unit 29, it is easy to grasp which kind of measurement method can be selected by the operator, which is user-friendly. However, the present invention is not limited to this. In a case where the apparatus side can recognize whether the measurement is a measurement in the horizontal direction or an area measurement, that is, in a case where measurement method information (preset type gesture (for example, finger movement)) can be recognized on the apparatus side, for example, a warning such as "This measurement target cannot be measured in the horizontal direction" or "The area of this measurement target cannot be measured" may be given. In this case, it is assumed that the operator has knowledge about the type of measurement method. As a specific method for the above recognition, for example, a gesture type can be stored in a storage unit (not shown) and can be compared with the gesture input by the operator for recognition.

The warning notification unit 38 may provide visual notification by changing and displaying the color of the GUI, or may provide audible notification by sound using a speaker (not shown) or the like, or may provide tactile notification by vibration using a vibration unit (not shown) or the like, and the notification method can be appropriately changed. The function of the warning notification unit 38 is realized by the control unit 35 similarly to the notification unit 37, for example. The vibration unit is configured by, for example, a vibration motor. Thus, by comprising the warning notification unit 38, the operator can quickly change the wrong measurement method.

Figure 16:
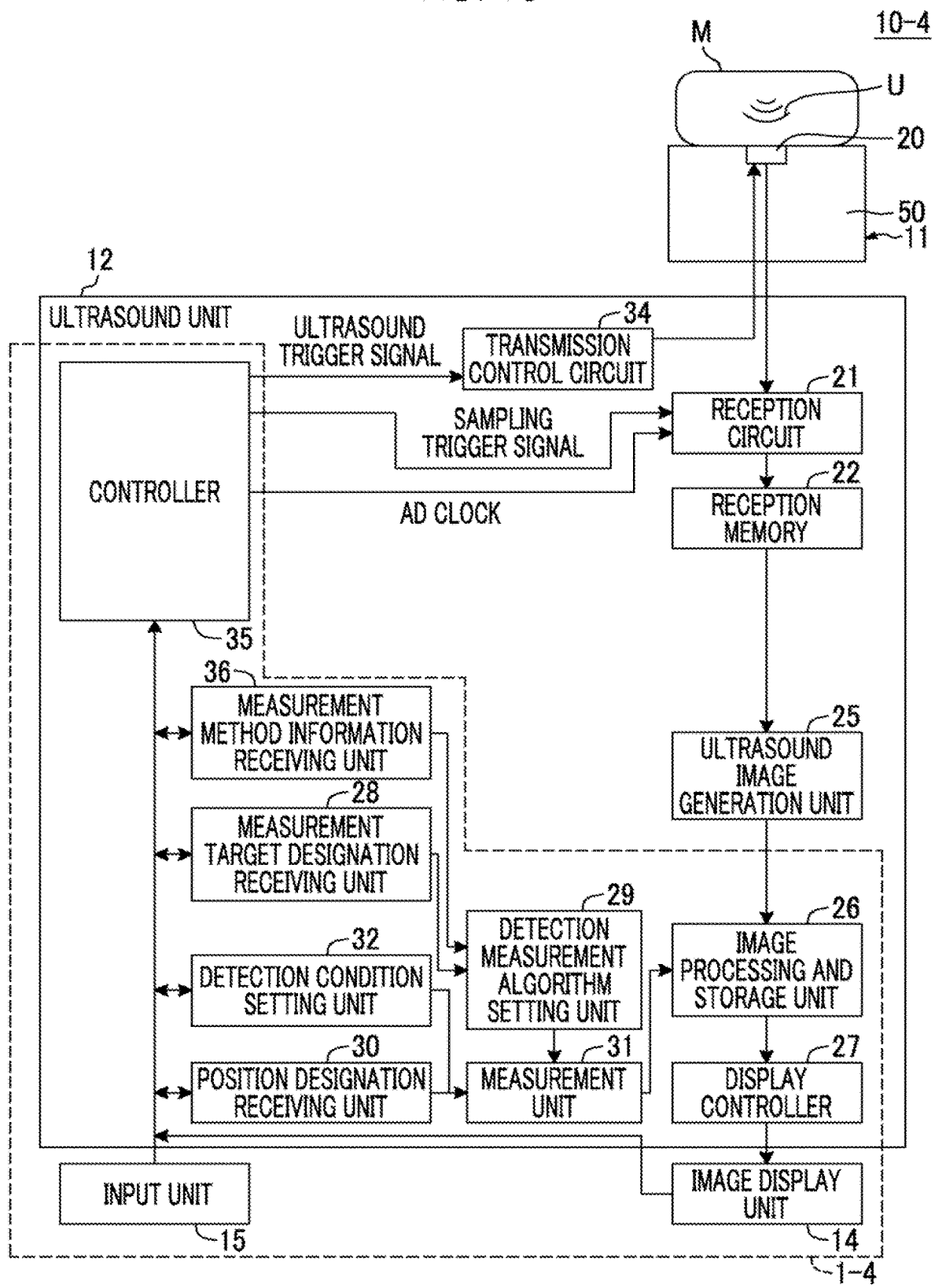
FIG. 16 is a schematic diagram showing the overall configuration of an acoustic wave image capturing apparatus comprising an acoustic wave measurement apparatus according to a fourth embodiment of the present invention.
Figure 17:
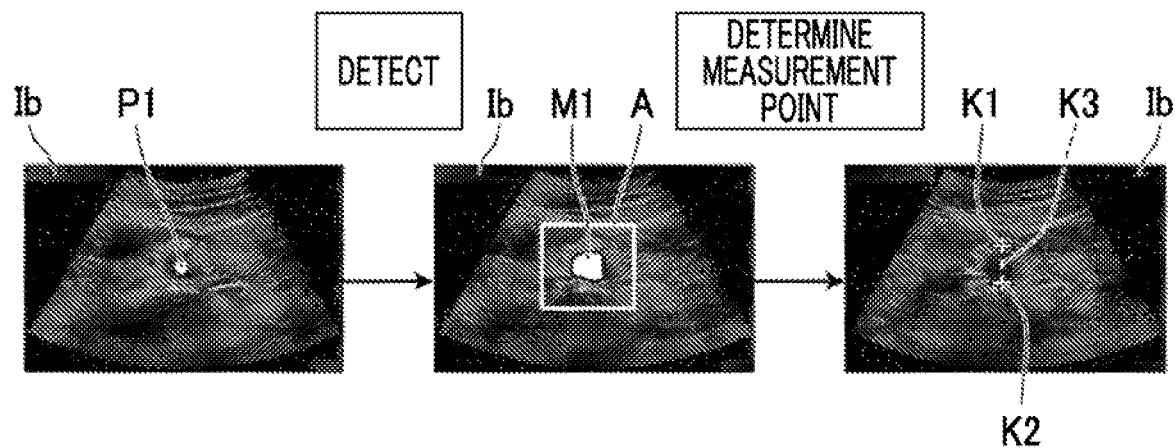
FIG. 17 is a diagram illustrating processing by the acoustic wave measurement apparatus shown in FIG. 16.
Figure 18:
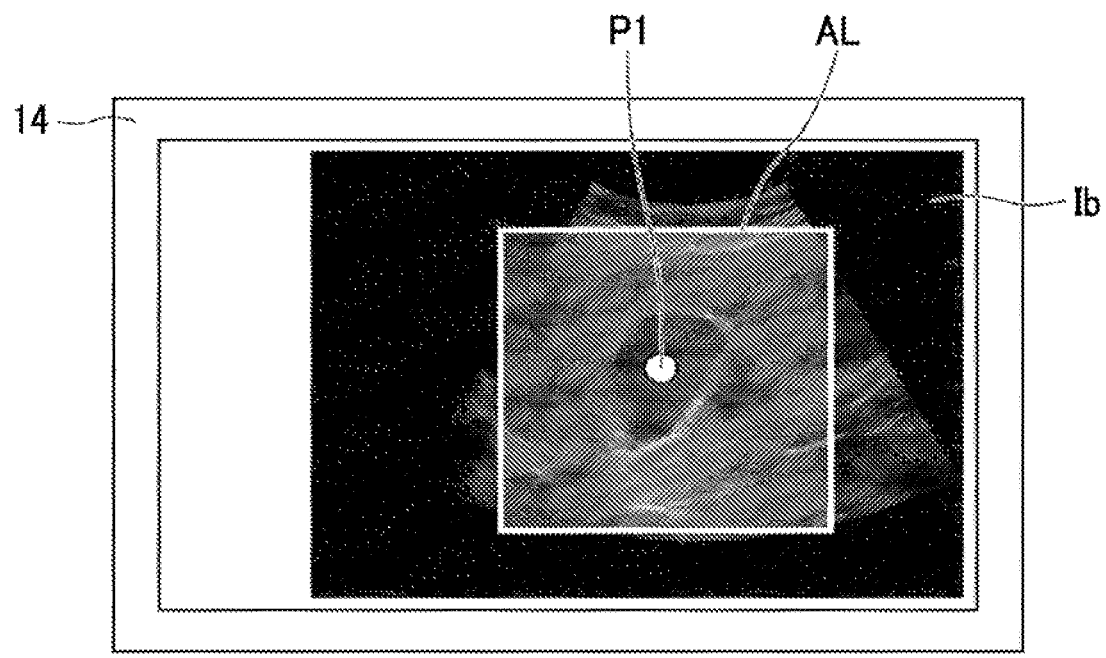
FIG. 18 is a diagram showing an example of the size of a detection range on an ultrasound image.
Figure 19:
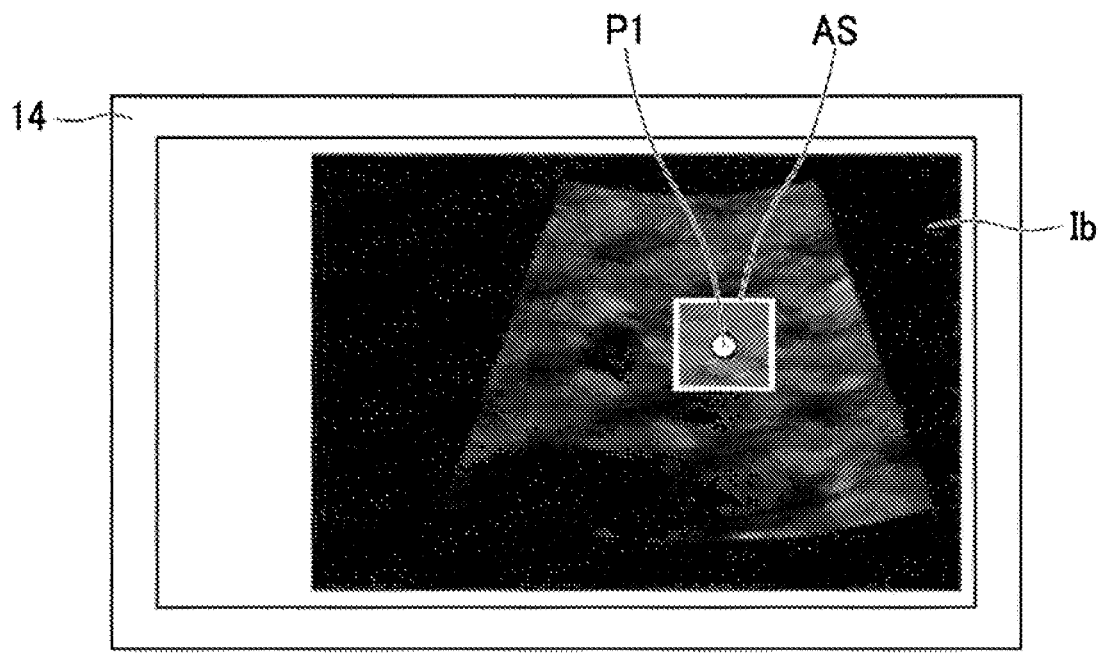
FIG. 19 is a diagram showing another example of the size of the detection range on the ultrasound image.
Figure 20:
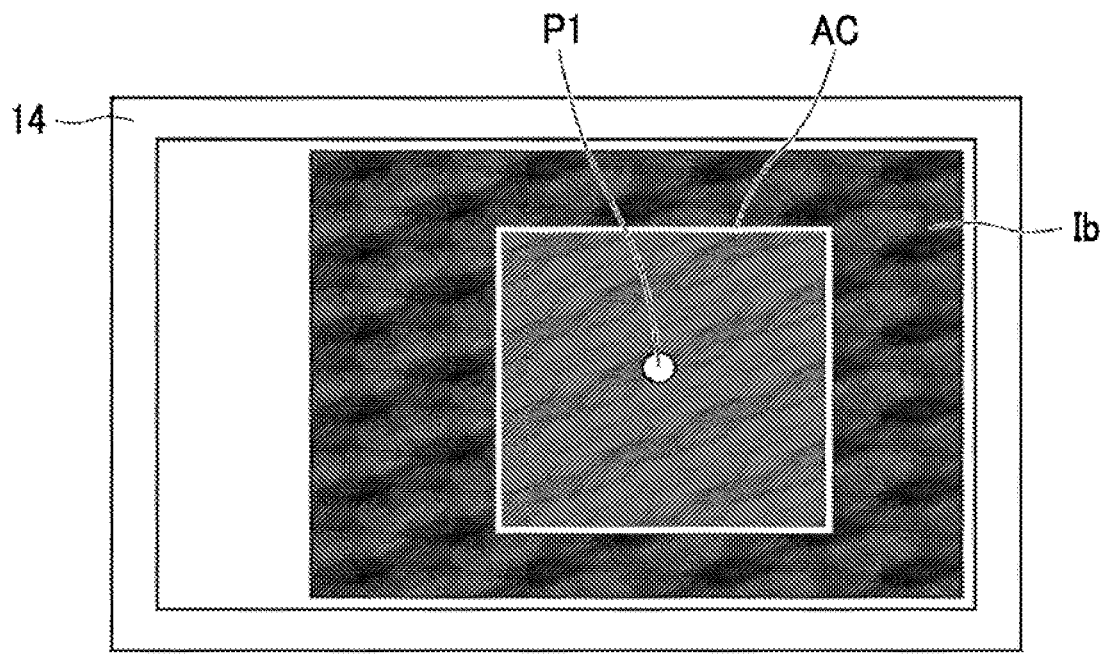
FIG. 20 is a diagram showing an example of the position of a detection range on the ultrasound image.
Figure 21:
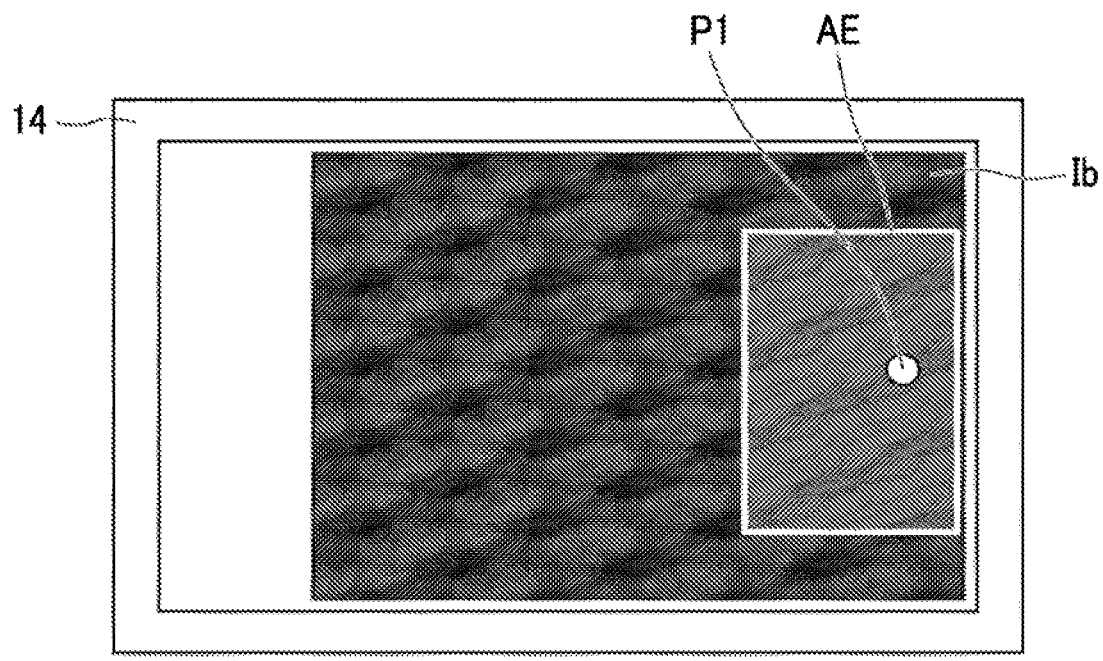
FIG. 21 is a diagram showing another example of the position of the detection range on the ultrasound image.
Figure 22:
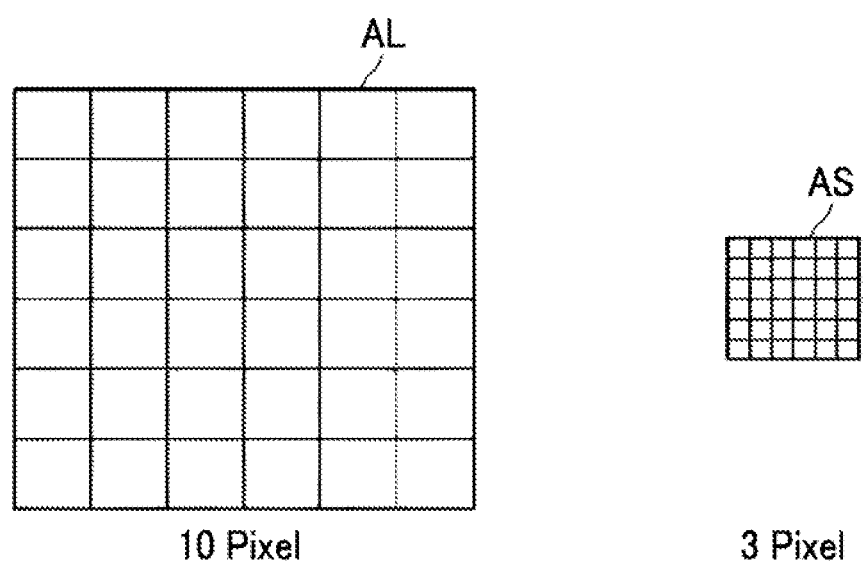
FIG. 22 is a diagram illustrating the detection accuracy within the detection range.
Figure 23:
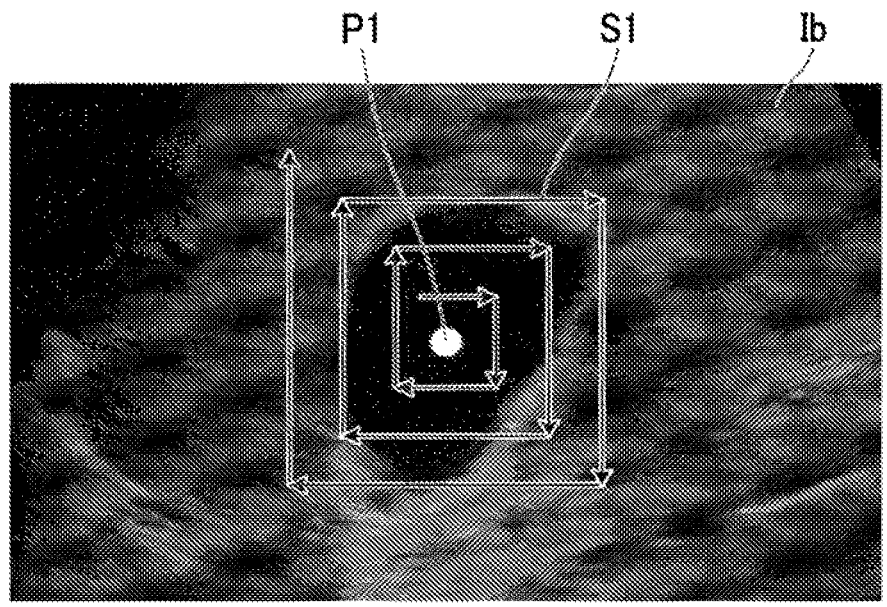
FIG. 23 is a diagram showing an example of the detection order on the ultrasound image.
Figure 24:
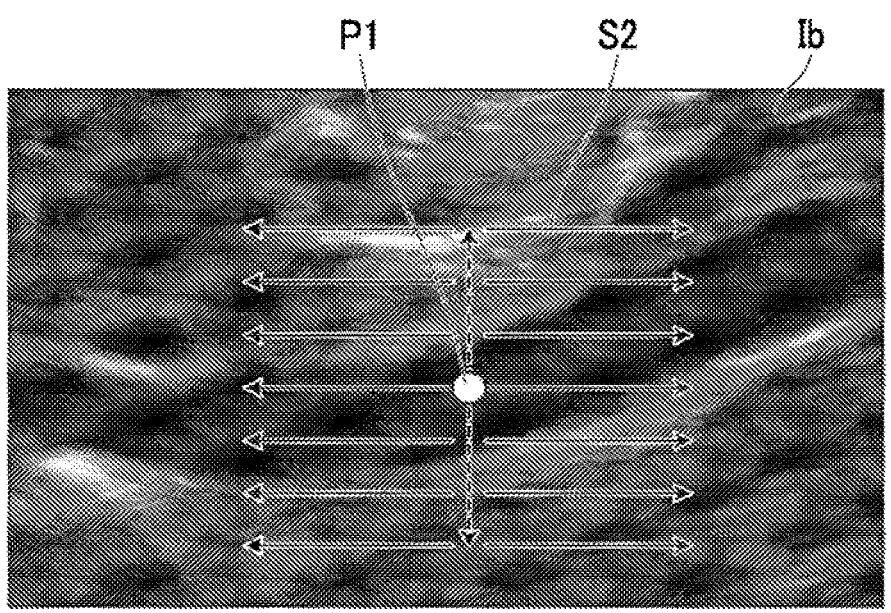
FIG. 24 is a diagram showing another example of the detection order on the ultrasound image.

Next, an acoustic wave image capturing apparatus 10-4 comprising an acoustic wave measurement apparatus 1-4 according to a fourth embodiment of the present invention will be described in detail with reference to the diagrams. FIG. 16 is a schematic diagram showing the overall configuration of the acoustic wave image capturing apparatus 10-4 comprising the acoustic wave measurement apparatus 1-4 according to the fourth embodiment of the present invention. FIG. 17 is a diagram illustrating processing by the acoustic wave measurement apparatus 1-4 shown in FIG. 16. FIG. 18 is a diagram showing an example of the size of a detection range on the ultrasound image Ib. FIG. 19 is a diagram showing another example of the size of the detection range on the ultrasound image Ib. FIG. 20 is a diagram showing an example of the position of the detection range on the ultrasound image Ib. FIG. 21 is a diagram showing another example of the position of the detection range on the ultrasound image Ib. FIG. 22 is a diagram illustrating the detection accuracy within the detection range. FIG. 23 is a diagram showing an example of the detection order on the ultrasound image Ib. FIG. 24 is a diagram showing another example of the detection order on the ultrasound image Ib. The acoustic wave measurement apparatus 1-4 shown in FIG. 16 is obtained by further providing a detection condition setting unit 32 in the acoustic wave measurement apparatus 1 shown in FIG. 2, and the other components are the same as those of the acoustic wave measurement apparatus 1 shown in FIG. 2. Therefore, the same components are denoted by the same reference numerals for the sake of convenience, and the description thereof will be omitted herein.

The acoustic wave measurement apparatus 1-4 shown in FIG. 16 comprises the detection condition setting unit 32. The detection condition setting unit 32 determines at least one of the position, size, detection accuracy, or detection order of the detection range A of the measurement target M1 based on at least one of a position P1 on the ultrasound image Ib shown in FIG. 17 received by the position designation receiving unit 30 or the measurement item received by the measurement target designation receiving unit 28. For example, the function of the detection condition setting unit 32 is realized by the program being operated by the control unit 35 configured by a processor.

Specifically, the detection condition setting unit 32 determines the size of the detection range A of the measurement target M1 based on the measurement item. For example, in a case where the measurement target M1 is a relatively large organ, such as a kidney, the measurement unit 31 detects, for example, a quadrangular detection range AL of 100 pixels vertically and horizontally with the received position P1 as the center, as shown in FIG. 18.

On the other hand, in a case where the measurement target M1 is a relatively small organ, such as the common bile duct or aorta, the measurement unit 31 detects, for example, a quadrangular detection range AS of 20 pixels vertically and horizontally with the received position P1 as the center, as shown in FIG. 19. Since the range in which the presence of the measurement target M1 is assumed differs depending on the size of the measurement target M1, the processing time required to detect the measurement target M1 can be shortened by changing the size of the detection range A according to the size of the measurement target M1.

The detection condition setting unit 32 determines the position of the detection range A of the measurement target M1 based on the position P1 on the ultrasound image Ib shown in FIG. 17 received by the position designation receiving unit 30. For example, as shown in FIG. 20, in a case where the position P1 is present near the center of the ultrasound image Ib, the measurement unit 31 detects a quadrangular detection range AC that is vertically and horizontally symmetrical with the position P1 as the center.

On the other hand, for example, as shown in FIG. 21, in a case where the position P1 is present near the right end portion of the ultrasound image Ib, the measurement unit 31 detects a quadrangular detection range AE that is vertically symmetrical and horizontally asymmetrical so as not to protrude from the ultrasound image Ib with the position P1 as the center. Since the range in which the presence of the measurement target M1 is assumed differs depending on the size of the measurement target M1, the size of the detection range A may be reduced by changing the position of the detection range A according to the position P1 received by the position designation receiving unit 30. In a case where the size of the detection range A is reduced, the processing time required to detect the measurement target M1 can be shortened.

The detection condition setting unit 32 determines the detection accuracy of the detection range A of the measurement target M1 based on the measurement item. For example, in a case where the measurement target M1 is a relatively large organ, such as a kidney, the measurement unit 31 roughly detects, for example, six 10-pixel regions horizontally and six 10-pixel regions vertically in the detection range AL as shown in FIG. 22.

On the other hand, in a case where the measurement target M1 is a relatively small organ, such as the common bile duct or aorta, the measurement unit 31 finely detects, for example, six 3-pixel regions horizontally and six 3-pixel regions vertically in the detection range AS as shown in FIG. 22. Since the range in which the presence of the measurement target M1 is assumed differs depending on the size of the measurement target M1, the balance of the detection accuracy and the processing time required to detect the measurement target M1 and can be improved by changing the detection accuracy in the detection range A according to the size of the measurement target M1. In the present embodiment, in a case where the detection accuracy is changed based on the size of the measurement target M1, the size of the detection range is also changed based on the size of the measurement target M1. However, the present invention is not limited thereto, and only the detection accuracy may be changed.

The detection condition setting unit 32 determines the detection order of the measurement target M1 based on the position P1 received by the position designation receiving unit 30, the measurement target, and the measurement method received by the measurement method information receiving unit 36. For example, in a case where the measurement target are a round organ, such as a gallbladder short axis surface size or an abdominal aorta short axis diameter, detection is performed in the order indicated by a scanning line S1 in a spiral shape from the center toward the outside with the position P1 as the center, as shown in FIG. 23. The interval between the scanning lines S1 may be equal, or the interval may be increased toward the outside or can be appropriately changed. The scanning may be clockwise or counterclockwise, or can be appropriately changed. Although the spiral shape is set in the present embodiment, the present invention is not limited thereto. For example, a plurality of quadrangles whose sizes increase toward the outside with the position P1 as the center may be used as scanning lines. In this case, the interval between the scanning lines may be equal, or the interval may be increased toward the outside or can be appropriately changed. The scanning may be clockwise or counterclockwise, or the rotation direction may be changed for each quadrangle or can be appropriately changed. The shape of the scanning line is not limited to a quadrangle, and the shape can be appropriately changed.

On the other hand, in a case where the measurement target is a horizontally long organ, such as the inferior aorta or common bile duct, detection in the horizontal direction (arrow S2 in the diagram) is performed and then detection in the vertical direction is performed as shown in FIG. 24. In this case, detection in the horizontal direction passing through the position P1 is performed in the order of the left direction and the right direction, and then upward movement is made to perform detection in the horizontal direction in the order of the left direction and the right direction, and downward movement from the position P1 is made to perform detection in the horizontal direction in the order of the left direction and the right direction, so that the detection is performed in a direction away from the position P1 in the order of the upward direction and the downward direction. The order of detection is not limited thereto, and detection in the horizontal direction on the lower side may be performed after detection in the horizontal direction on the upper side is entirely performed, or the order of detection can be appropriately changed. By determining the detection order according to the shape of the measurement target M1, the speed of finding the measurement target M1 can be increased. In the present embodiment, the detection condition setting unit 32 changes the size or the detection accuracy of the detection range described above, and determines the detection order of the measurement target M1 based on the measurement target item and the measurement method and the position P1 received by the position designation receiving unit 30. However, the detection condition setting unit 32 according to the embodiment of the present invention is not limited thereto, and the detection condition setting unit 32 may change only the size or the detection accuracy of the detection range described above, or may determine only the detection order of the measurement target M1.

Figure 25:
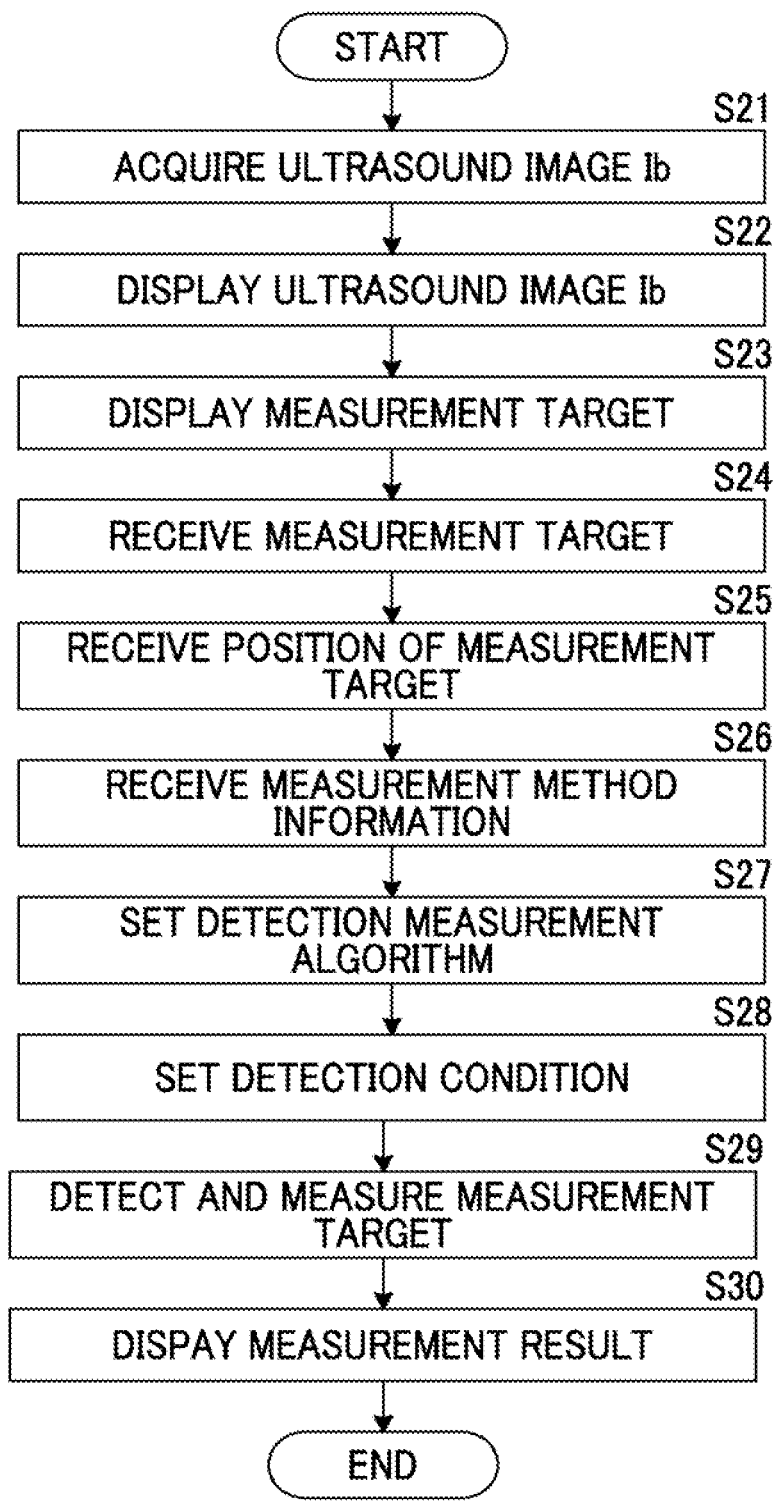
FIG. 25 is a flowchart showing a method of a series of processes of the acoustic wave measurement apparatus shown in FIG. 16.

Next, an operation method of an acoustic wave measurement apparatus, in which the acoustic wave measurement apparatus 1-4 measures a measurement target in the ultrasound image Ib displayed on the image display unit 14, in the acoustic wave image capturing apparatus 10-4 described above will be described. FIG. 25 is a flowchart showing a method of a series of processes of the acoustic wave measurement apparatus 1-4 shown in FIG. 16. Since steps S21 to S27 in FIG. 25 are the same as steps S1 to S17 in the flowchart of FIG. 8, the description thereof will be omitted herein.

In the acoustic wave measurement apparatus 1-4, as shown in FIG. 25, in a case where the detection measurement algorithm is set by the detection measurement algorithm setting unit 29 (step S27), the detection condition setting unit 32 determines at least one of the position, size, detection accuracy, or detection order of the detection range A of the measurement target M1 as described above based on at least one of the position P1 on the ultrasound image Ib received by the position designation receiving unit 30, the measurement target received by the measurement target designation receiving unit 28, or the measurement method received by the measurement method information receiving unit 36 (step S28). Then, the measurement unit 31 detects the inside of the detection range set by the detection condition setting unit 32 based on the detection algorithm set by the detection measurement algorithm setting unit 29, and detects the accurate position and region of the measurement target M1 on the ultrasound image Ib. As shown in FIG. 17, the measurement unit 31 determines the optimal measurement points K1 and K2 for the detected measurement target M1, and measures the length of the line K3 connecting the measurement points K1 and K2 to each other (step S29). Then, the measurement unit 31 displays the measurement points K1 and K2 and the line K3, the measurement target M1 and the size or length of the measurement target M1 as the measurement result R, and the like on the image display unit 14 through the image processing and storage unit 26 and the display control unit 27 (step S30). As described above, the acoustic wave measurement apparatus 1-4 measures the measurement target.

The notification unit 37 or the warning notification unit 38 described above may be further provided in the acoustic wave measurement apparatus 1-4 of the present embodiment.

Up to now, the embodiments in which only the ultrasound image Ib is displayed as an acoustic wave image in the present invention has been described. However, even in a case where a photoacoustic wave image is displayed as an acoustic wave image, the effect of the present invention can be obtained. In addition, as an acoustic wave image, a composite image obtained by superimposing an ultrasound image and a photoacoustic wave image may be displayed. Also in this case, the effect of the present invention can be obtained.

The acoustic wave measurement apparatus according to the embodiment of the present invention is not limited to the embodiments described above, and can be appropriately changed without departing from the spirit of the invention.

EXPLANATION OF REFERENCES 1, 1-2, 1-3, 1-4: acoustic wave measurement apparatus
10, 10-2, 10-3, 10-4 acoustic wave image capturing apparatus
10C: housing
11: probe
12: ultrasound unit
14: image display unit
15: input unit (touch panel)

20: transducer array
21: reception circuit
22: reception memory
25: ultrasound image generation unit
26: image processing and storage unit
27: display control unit
28: measurement target designation receiving unit
29: detection measurement algorithm setting unit
30: position designation receiving unit
31: measurement unit
32: detection condition setting unit
34: transmission control circuit
35: control unit
36: measurement method information receiving unit
37: notification unit
38: warning notification unit
40: light emitting unit
50: housing
Ib: ultrasound image
M: subject
M1: measurement target
N: list of measurement targets
P: finger of operator

What is claimed is:

1. An operation method of an acoustic wave measurement apparatus comprising an touch-panel image display, and a processor, the method comprising:
    causing the touch-panel image display to display an acoustic wave image;
    causing the processor:
        to receive designation of a measurement target via the touch-panel image display;
        to receive designation of a position of a measurement target on the acoustic wave image displayed on the touch-panel image display via the touch-panel image display;
        to receive input of movement of a finger of an operator, the movement of the finger comprises dragging and/or selecting a plurality of coordinates as a first set of coordinate information;
        to determine measurement method information indicating a measurement method desired by the operator based on the received first set of coordinate information;
        to set a detection measurement algorithm based on the measurement target and the measurement method information; and
        to detect the measurement target based on the position and the detection measurement algorithm, generate a second set of coordinate information, optimized from the first set of coordinate information, of the measurement target by using the detection measurement algorithm, and perform measurement for the detected measurement target using the second set of coordinate information.

2. The operation method of the acoustic wave measurement apparatus according to claim 1,
    wherein reception of designation of the position and reception of the measurement method information are separate.

3. The operation method of the acoustic wave measurement apparatus according to claim 2,
    wherein the processor determines a position of a detection range in which the detection is performed based on the position.

4. The operation method of the acoustic wave measurement apparatus according to claim 2,
    wherein the processor determines a measurement position where the measurement is performed based on the position.

5. The operation method of the acoustic wave measurement apparatus according to claim 2,
    wherein, when there is only one measurement method capable of measuring the measurement target, the processor neglects the measurement method information and sets the detection measurement algorithm based on the measurement method capable of measuring the measurement target.

6. The operation method of the acoustic wave measurement apparatus according to claim 2,
    wherein the processor further:
        when there is only one measurement method capable of measuring the measurement target, provides notification of information indicating the measurement method capable of measuring the measurement target.

7. The operation method of the acoustic wave measurement apparatus according to claim 1,
    wherein reception of designation of the position and reception of the measurement method information are integrated.

8. The operation method of the acoustic wave measurement apparatus according to claim 7,
    wherein the processor determines a position of a detection range in which the detection is performed based on the position.

9. The operation method of the acoustic wave measurement apparatus according to claim 7,
    wherein the processor determines a measurement position where the measurement is performed based on the position.

10. The operation method of the acoustic wave measurement apparatus according to claim 7,
    wherein, when there is only one measurement method capable of measuring the measurement target, the processor neglects the measurement method information and sets the detection measurement algorithm based on the measurement method capable of measuring the measurement target.

11. The operation method of the acoustic wave measurement apparatus according to claim 1,
    wherein the processor is configured to determine a position of a detection range in which the detection is performed based on the position.

12. The operation method of the acoustic wave measurement apparatus according to claim 1,
    wherein the processor determines a measurement position where the measurement is performed based on the position.

13. The operation method of the acoustic wave measurement apparatus according to claim 1,
    wherein, when there is only one measurement method capable of measuring the measurement target, the processor neglects the measurement method information and sets the detection measurement algorithm based on the measurement method capable of measuring the measurement target.

14. The operation method of the acoustic wave measurement apparatus according to claim 1,
    wherein the processor further:
        when there is only one measurement method capable of measuring the measurement target, provides notification of information indicating the measurement method capable of measuring the measurement target.

15. The operation method of the acoustic wave measurement apparatus according to claim 1,
   wherein the processor further:
   gives a warning when a detection measurement algorithm based on the measurement method information is not able to be set.

16. The operation method of the acoustic wave measurement apparatus according to claim 1,
   wherein the processor further:
   sets conditions, under which the detection for the measurement target is performed, based on at least one of the position or the measurement target,
   wherein the processor performs detection based on the conditions that are set.

17. The operation method of the acoustic wave measurement apparatus according to claim 16,
   wherein the processor sets at least one of a shape of a detection range, a size of the detection range, a detection accuracy, or a detection order as conditions for performing the detection.

18. The operation method of the acoustic wave measurement apparatus according to claim 1,
   wherein the acoustic wave image is an ultrasound image.

19. The operation method of the acoustic wave measurement apparatus according to claim 1,
   wherein the acoustic wave image is a photoacoustic wave image.

\* \* \* \* \*